(12) United States Patent
Smith, III et al.

(10) Patent No.: US 8,193,241 B2
(45) Date of Patent: Jun. 5, 2012

(54) DISCODERMOLIDE ANALOGUES AND METHODS OF THEIR USE

(75) Inventors: Amos B. Smith, III, Merion, PA (US); Simon J. Shaw, San Francisco, CA (US); David C. Myles, Berkeley, CA (US)

(73) Assignee: The Trustees Of The University Of Pennsylvania, Philadelphia, PA (US)

( * ) Notice: Subject to any disclaimer, the term of this patent is extended or adjusted under 35 U.S.C. 154(b) by 0 days.

(21) Appl. No.: 12/946,280

(22) Filed: Nov. 15, 2010

(65) Prior Publication Data
US 2011/0172220 A1    Jul. 14, 2011

Related U.S. Application Data

(63) Continuation of application No. 12/664,973, filed as application No. PCT/US2008/068288 on Jun. 26, 2008, now abandoned.

(60) Provisional application No. 60/946,883, filed on Jun. 28, 2007.

(51) Int. Cl.
| C07D 215/227 | (2006.01) |
| C07D 265/36 | (2006.01) |
| C07D 311/22 | (2006.01) |
| A61K 31/538 | (2006.01) |
| A61K 31/353 | (2006.01) |
| A61K 31/4704 | (2006.01) |

(52) U.S. Cl. ........................ 514/457; 549/399
(58) Field of Classification Search .................. 549/399; 514/457
See application file for complete search history.

(56) References Cited

U.S. PATENT DOCUMENTS
| 6,734,177 B2 | 5/2004 | Kinder et al. |
| 6,844,357 B2 | 1/2005 | Yang |
| 2005/0090526 A1 | 4/2005 | Cai |
| 2005/0101662 A1 | 5/2005 | Jacobs |

FOREIGN PATENT DOCUMENTS
WO    WO 2009/006184    1/2009

OTHER PUBLICATIONS

Belliotti, et al., "A Series of 6- and 7-Piperazinyl- and—Piperidinylmethylbenzoxazinones with Dopamine D4 Antagonist Activity: Discovery of a Potential Atypical Antipsychotic Agent", J. Med. Chem., Dec. 16, 1999, 42(25), 5181-5187.

Gunasekera, et al., "Discordermolide: A New Bioactive Polyhydroxylated Lactone From the Marine Sponge Discodermia Dissolute", J. Org. Chem. Aug. 1990, 55(16), 4912-4915.
Gunasekera, et al., "Discordermolide: A New Bioactive Polyhydroxylated Lactone From the Marine Sponge Discodermia Dissolute", J. Org. Chem. Aug. 1990, 55(16), 4912-4915. Correction: J. Org. Chem. Feb. 1991, 56(3) 1346-1349.
Mickel, et al., "Large-Scale Synthesis of the Anti-Cancer Marine Natural Product (+)-Discordermolide. Part 5: Linkage of Fragments $C_{1-6}$ and $C_{7-24}$ and Finale", Org. Process Res. Dev., Jan. 2004, 8(1), 122-130.
Paterson et al., "The Development of a Practical Total Synthesis of Discodermolide, A Promising Microtubule-Stabilizing Anticancer Agent", Eur. J. Org. Chem., Jun. 2003, 12, 2193-2208.
Paterson et al., "Development of a Third-Generation Total Synthesis of (+)-Discodermolide: an Expedient Still-Gennari-Type Fragment Coupling Utilizing an Advanced Beta-Ketophosphonate", J. Org. Chem., Jul. 8, 2005, 70(14), 5494-5507.
Smith, III, et al., "Design, Synthesis, and Biological Evaluation of Simplified Analogues of (+)-Discodermolide. Additional Insights on the Importance of the Diene, the C(7) Hydroxyl, and the Lactone", Org. Lett., Nov. 10, 2005, 7(23), 5229-5232.
Smith, III, et al., "A Practical Improvement, Enhancing the Large-Scale Synthesis of (+)-Discodermolide: A Third-Generation Approach", Org. Lett., Nov. 13, 2003, 5(23), 4405-4408.
Smith, III, et al., "Total Synthesis of (+)-Discodermolide: A Highly Convergent Fourth-Generation Approach", Org. Lett., Apr. 28, 2005, 7(9), 1825-1828.
Smith, III, et al., "Evolution of a Gram-Scale Synthesis of (+)-Discodermolide", J. Am. Chem. Soc, Aug. 26, 2000, 122(36), 8654-8664.
ter Haar et al., "Discodermolide, A Cytotoxic Marine Agent That Stabilizes Microtubules More Potently Than Taxol", Biochemistry, Jan. 9, 1996, 35(1), 243-250.
International Patent Application No. PCT/US2008/068288: International Search Report dated Sep. 25, 2008, 1 page.

*Primary Examiner* — Kahsay T Habte
(74) *Attorney, Agent, or Firm* — Woodcock Washburn, LLP

(57) ABSTRACT

6- and 7-substituted coumarin and related 6- and 7-substituted 1H-quinolin-2-one compounds, pharmaceutical compositions containing these compounds, and methods for their pharmaceutical use are disclosed. In certain embodiments, the 7-substituted coumarin and related 7-substituted 1H-quinolin-2-one compounds mimic or exceed the high level of pharmacological activity of discodermolide. In other embodiments, their preparation involves more readily available materials, higher yield processes and/or simpler synthetic sequences. In yet other embodiments, the compounds of the invention represent structurally simpler, therapeutically active analogues of discodermolide than heretofore known and may be useful as microtubule stabilizers and, inter alia, for treating and/or preventing cancer and other diseases, disorders, and/or conditions mediated by the stabilization of microtubules.

19 Claims, No Drawings

DISCODERMOLIDE ANALOGUES AND METHODS OF THEIR USE

CROSS-REFERENCE TO RELATED APPLICATIONS

This application is a continuation of U.S. patent application Ser. No. 12/664,973, filed Dec. 16, 2009 which is a National Stage of International Application No. PCT/US2008/068288, filed Jun. 26, 2008, which claims the benefit of U.S. Provisional Application No. 60/946,883, filed Jun. 28, 2007, the disclosures of which are incorporated herein by reference in their entireties.

GOVERNMENT SUPPORT

This work was supported by a grant from the National Institutes of Health (GM029028). Pursuant to 35 U.S.C. § 202, the government may have certain rights in the invention.

FIELD OF THE INVENTION

This invention relates to compounds and their compositions which mimic the chemical and/or biological activity of discodermolide, and to methods of their use.

BACKGROUND OF THE INVENTION

In 1990, Gunasekera and co-workers at the Harbor Branch Oceanographic Institute reported the isolation of (+)-discodermolide (1), an architecturally novel metabolite of the marine sponge *Discodermia dissoluta* (0.002% w/w). (See, Gunasekera, et al., J. Org. Chem. 1990, 55, 4912. Correction: J. Org. Chem. 1991, 56, 1346).

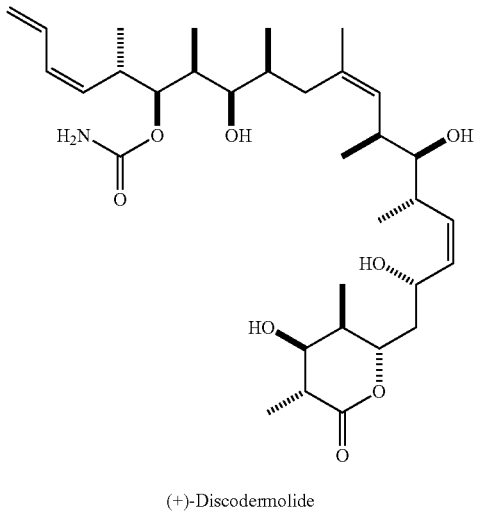

(+)-Discodermolide

This marine natural product, a potent stabilizer of microtubules, leads to cell cycle arrest, and ultimately apoptosis—a mechanism similar to the anticancer agents paclitaxel and the epothilones (E. ter Haar, R. J. Kowalski, E. Hamel, C. M. Lin, R. E. Longley, S. P. Gunasekera, H. S. Rosenkranz and B. W. Day, *Biochemistry*, 1996, 35, 243-250. Discodermolide 1 however is only available in small quantities from the sponge *Discodermia dissoluta*, and neither the producing organism (thought to be a symbiont) has been cultured, nor have the genes responsible for biosynthesis been obtained. Thus, the large quantities required for clinical trial may be obtained through complex total synthesis routes (See (a) A. B. Smith, III, T. J. Beauchamp, T. J.; M. J. LaMarche, M. D. Kaufman, Y. Qui, H. Arimoto, D. R. Jones and K. Kobayashi, *J. Am. Chem. Soc.,* 2000, 122, 8654-8664; (b) A. B. Smith, III, B. S. Freeze, M. Xian and T. Hirose, *Org. Lett.,* 2005, 7, 1825-1828; (c) I. Paterson and G. J. Florence, *Eur. J. Org. Chem.,* 2003, 2193-2208; (d) I. Paterson and I. Lyothier, *J. Org. Chem.,* 2005, 70, 5494-5507; (e) S. J. Mickel, D. Niederer, R. Daeffler, A. Osmani, E. Kuesters, E. Schmid, K. Schaer and R. Gamoni, *Org. Process Res. Dev.,* 2004, 8, 122-130.

Therefore, there is a need for improved compounds and their compositions that mimic or exceed the high level of pharmacological activity of discodermolide, whose preparation involves more readily available materials, higher yield processes and/or simpler synthetic sequences, or whose products represent structurally simpler discodermolide analogues. The present invention is directed to these compounds, their pharmaceutical compositions, and methods of their use as well as other important ends.

Importantly, the congeners of the present invention represent structurally simple discodermolide analogues with nanomolar antiproliferative activity in cell culture. Compared to (+)-discodermolide, these molecules are considerably easier to synthesize, which may reduce the time and cost of a large scale synthesis.

SUMMARY OF THE INVENTION

Accordingly, the present invention is directed, in part, to 6- and 7-substituted coumarin and related 6- and 7-substituted 1H-quinolin-2-one compounds. In preferred form, the novel compounds of the invention have the following formulae I or Ia:

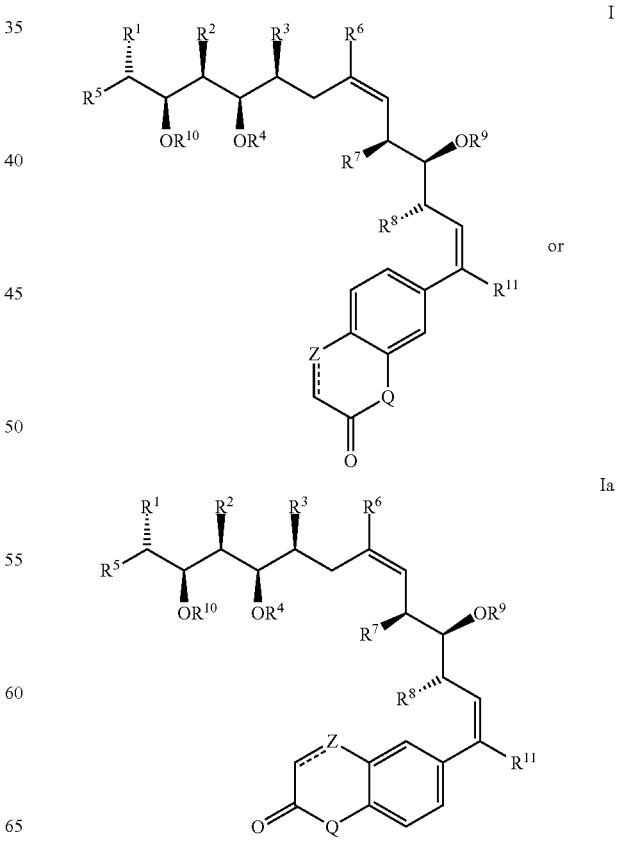

wherein:

----- represents the presence of a single bond or double bond;

$R^1$, $R^2$, $R^3$, $R^6$, $R^7$, $R^8$, and $R^{11}$ are each independently H or $C_{1-10}$alkyl;

$R^4$ and $R^9$ are each independently H or acid labile protecting group;

$R^5$ is $C_{2-6}$monoalkenyl or $C_{4-6}$alkadienyl;

$R^{10}$ is H, —C(=O)$NR^{13}R^{14}$, or oxidatively labile hydroxyl protecting group;

Q is —O— or —$NR^{12}$;

Z is —CH—, —$CH_2$—, or —O—, provided that when ----- represents a double bond, then Z is —CH—;

$R^{12}$ is H, alkyl, or acid labile amino protecting group;

$R^{13}$ and $R^{14}$ are each independently H, $C_{1-10}$alkyl, $C_{2-6}$alkenyl, $C_{2-6}$alkynyl, $OR^c$, C(=O)$R^b$, S(O)$_pR^b$, $(CH_2)_r$$C_{3-12}$carbocycle, or $(CH_2)_r$heterocycle having 5 to 12 ring atoms; or $R^{13}$ and $R^{14}$ taken together with the nitrogen atom to which they are attached form a 5- or 6-membered heterocycle containing 0-3 additional heteroatoms selected from O, S, and N;

$R^b$ and $R^c$ are each independently H, $C_{1-6}$alkyl, $C_{2-6}$alkenyl, $C_{2-6}$alkynyl, $C_{3-6}$cycloalkyl, or $(CH_2)_r$phenyl;

p is 1 or 2; and each r is independently 0, 1, 2, 3, or 4;

or a pharmaceutically acceptable salt thereof.

In other embodiments, the present invention is directed to pharmaceutical compositions, comprising a pharmaceutically acceptable carrier therapeutically effective amount of a compound according to formula I or Ia or a pharmaceutically acceptable salt thereof.

In certain other embodiments, the present invention is directed to methods for stabilizing microtubules, the method comprising administering to a patient in need thereof a therapeutically effective amount of a compound according to formula I or Ia.

These and other aspects of the invention will become more apparent from the following detailed description.

DETAILED DESCRIPTION OF ILLUSTRATIVE EMBODIMENTS

The invention relates to 6- and 7-substituted coumarin and related 6- and 7-substituted 1H-quinolin-2-one compounds, pharmaceutical compositions containing these compounds, and methods for their pharmaceutical use. In certain embodiments, the 6- and 7-substituted coumarin and related 6- and 7-substituted 1H-quinolin-2-one compounds possess antiproliferative activity, and/or stabilize microtubules, leading to cell cycle arrest, and ultimately apoptosis.

As employed above and throughout the disclosure, the following terms, unless otherwise indicated, shall be understood to have the following meanings.

As used herein, "alkyl" refers to an optionally substituted, saturated straight, or branched, hydrocarbon having from about 1 to about 10 carbon atoms (and all combinations and subcombinations of ranges and specific numbers of carbon atoms therein), preferably with from about 1 to about 6, more preferably 1 to about 4, yet more preferably about 1 to about 3, with methyl being most preferred. Alkyl groups include, but are not limited to, methyl, ethyl, n-propyl, isopropyl, n-butyl, isobutyl, t-butyl, n-pentyl, isopentyl, neopentyl, n-hexyl, isohexyl, 3-methylpentyl, 2,2-dimethylbutyl, and 2,3-dimethylbutyl.

As used herein, "alkenyl" refers to an optionally substituted alkyl group having from about 2 to about 10 carbon atoms and one or more double bonds (and all combinations and subcombinations of ranges and specific numbers of carbon atoms therein), wherein alkyl is as previously defined. In certain preferred embodiments, the alkenyl group contains from about 2 to about 6, more preferably about 3 to about 4, yet more preferably about 4. In other preferred embodiments, the alkenyl has one double bond, more preferably non-terminal.

As used herein, "alkynyl" refers to an optionally substituted alkyl group having from about 2 to about 10 carbon atoms and one or more triple bonds (and all combinations and subcombinations of ranges and specific numbers of carbon atoms therein), wherein alkyl is as previously defined.

As used herein, "cycloalkyl" refers to an optionally substituted, mono-, di-, tri-, or other multicyclic alicyclic ring system having from about 3 to about 20 carbon atoms (and all combinations and subcombinations of ranges and specific numbers of carbon atoms therein). In some preferred embodiments, the cycloalkyl groups have from about 3 to about 6 carbon atoms. Multi-ring structures may be bridged or fused ring structures, wherein the additional groups fused or bridged to the cycloalkyl ring may include optionally substituted cycloalkyl, aryl, heterocycloalkyl, or heteroaryl rings. Exemplary cycloalkyl groups include, but are not limited to, cyclopropyl, cyclobutyl, cyclopentyl, cyclohexyl, cyclooctyl, adamantyl, 2-[4-isopropyl-1-methyl-7-oxa-bicyclo[2.2.1]heptanyl], and 2-[1,2,3,4-tetrahydro-naphthalenyl].

A "carbocycle" comprises at least one ring formed entirely by carbon-carbon bonds (referred to herein as a carbocyclic ring), and does not contain a heterocycle. Unless otherwise specified, each ring within a carbocycle may be independently saturated, partially saturated or aromatic, and is optionally substituted as indicated. A carbocycle generally has from 1 to 3 fused, pendant or Spiro rings and optionally further contains one or more alkylene bridges; carbocycles within certain embodiments have one ring or two fused rings. Typically, each ring contains from 3 to 8 ring members (i.e., $C_3$-$C_8$); $C_3$-$C_6$ rings are recited in certain embodiments. Carbocycles comprising fused, pendant or spiro rings typically contain from 9 to 16 ring members. Certain representative carbocycles are cycloalkyl as described above (e.g., cyclohexyl, cycloheptyl or adamantyl). Other carbocycles are aryl (i.e., contain at least one aromatic carbocyclic ring, with or without one or more additional aromatic and/or cycloalkyl rings). Such aryl carbocycles include, for example, phenyl, naphthyl (e.g., 1-naphthyl and 2-naphthyl), fluorenyl, indanyl and 1,2,3,4-tetrahydronaphthyl.

A "heterocycle" has from 1 to 3 fused, pendant or spiro rings, at least one of which is a heterocyclic ring (i.e., one or more ring atoms is a heteroatom independently chosen from O, S and N, with the remaining ring atoms being carbon). Additional rings, if present, may be heterocyclic or carbocyclic. Typically, a heterocyclic ring comprises 1, 2, 3 or 4 heteroatoms; within certain embodiments each heterocyclic ring has 1 or 2 heteroatoms per ring. Each heterocyclic ring generally contains from 3 to 8 ring members (rings having from 4 or 5 to 7 ring members are recited in certain embodiments) and heterocycles comprising fused, pendant or spiro rings typically contain from 9 to 14 ring members. Certain heterocycles comprise a sulfur atom as a ring member; in certain embodiments, the sulfur atom is oxidized to SO or $SO_2$. Unless otherwise specified, a heterocycle may be a heterocycloalkyl group (i.e., each ring is saturated or partially saturated), such as a 4- to 7-membered heterocycloalkyl, which generally comprises 1, 2, 3 or 4 ring atoms that are independently chosen from C, O, N and S; or a heteroaryl group (i.e., at least one ring within the group is aromatic), such as a 5- to 10-membered heteroaryl (which may be monocyclic or bicyclic) or a 6-membered heteroaryl (e.g., pyridyl or pyrimidyl). N-linked heterocyclic groups are linked via a component nitrogen atom. In certain embodiments, heterocycles having 5 to 12 ring atoms are preferred. In other embodiments, heterocycles with 5 to 6 ring atoms are preferred.

As used herein, the term "oxidatively labile hydroxyl protecting group" means those hydroxyl protecting groups removable by an oxidizing agent such as 2,3-dichloro-5,6-dicyano-1,4-benzoquinone ("DDQ"). A non-limiting example of an oxidatively labile hydroxyl protecting group is a p-methoxybenzyl ("PMB" or "MPM") ether group.

As used herein, the term "acid labile hydroxyl protecting group" means an oxygen-bound group that can be removed upon exposure to an acid. Specific examples include, but are not limited to, BOM, acetyl, MOM, MEM, SEM, TBS, triethylsilyl, t-butyldiphenylsilyl, triisopropylsilyl, allyl and tetrahydropyranyl groups.

As used herein, the term "acid labile amino protecting group" means an nitrogen-bound group that can be removed upon exposure to an acid. Specific examples include, but are not limited to, Tmoc, Teoc, Adpoc, t-Bumeoc, BOC, Adoc, Voc, Moz, formamide, acetamide, benzamide, trityl, BOM, MOM, MEM, SEM, TBS, triethylsilyl, t-butyldiphenylsilyl, triisopropylsilyl, and allyl groups.

As will be readily understood, functional groups present may contain protecting groups during the course of synthesis. Protecting groups are known per se as chemical functional groups that can be selectively appended to and removed from functionalities, such as hydroxyl groups, amino groups and carboxyl groups. These protecting groups are present in a chemical compound to render such functionality inert to chemical reaction conditions to which the compound is exposed. Any of a variety of protecting groups may be employed with the present invention. Preferred protecting groups include: benzyloxycarbonyl, tert-butyloxycarbonyl group, trityl, BOM, acetyl, MOM, MEM, SEM, TBS, triethylsilyl, t-butyldiphenylsilyl, triisopropylsilyl, allyl and tetrahydropyranyl groups. Other preferred protecting groups that may be employed in accordance with the present invention may be described in Greene, T. W. and Wuts, P. G. M., *Protective Groups in Organic Synthesis* 2d. Ed., Wiley & Sons, 1991 or Philip J. Kocienski, "*Protecting Groups*", 2$^{nd}$ ed., John Wiley & Sons, Inc., New York (2005), along with teachings regarding their manner of use. In some cases, further organic transformations may be performed using methods well known to those of ordinary skill in the art, such as methods described in Richard C. Larock, "Comprehensive Organic Transformation," (VCH Publisher, Inc. 1989), the disclosures of which are incorporated herein by reference, in their entireties.

In some embodiments it is preferable to preserve the chemical distinctiveness between acid labile hydroxyl protecting groups $R^4$, $R^9$, oxidatively labile protecting group $R^{10}$, and acid labile amino protecting group $R^{12}$. Preferably, therefore in some embodiments, the acid labile hydroxyl protecting groups should not be oxidatively labile, and vice-versa.

Typically, substituted chemical moieties include one or more substituents that replace hydrogen. Exemplary substituents include, for example, halo (e.g., F, Cl, Br, I), alkyl, hydroxyl (—OH), oxo (=O), nitro (—NO$_2$), cyano (—CN), amino (—NH$_2$), —N-substituted amino (—NHR"), —N,N-disubstituted amino (—N(R")R"), carboxy (—COOH), —O—C(=O)R", —C(=O)R", —OR", —C(=O)OR", —NHC(=O)R", aminocarbonyl (—C(=O)NH$_2$), —N-substituted aminocarbonyl (—C(=O)NHR"), —N,N-disubstituted aminocarbonyl (—C(=O)N(R")R"), and the like.

A "therapeutically effective amount" (or dose) is an amount that, upon administration to a patient, results in a discernible patient benefit (e.g., provides detectable relief from at least one condition being treated). It will be apparent that the discernible patient benefit may be apparent after administration of a single dose, or may become apparent following repeated administration of the therapeutically effective dose according to a predetermined regimen, depending upon the indication for which the compound is administered.

As used herein, "pharmaceutically acceptable" refers to those compounds, materials, compositions, and/or dosage forms which are, within the scope of sound medical judgment, suitable for contact with the tissues of human beings and animals without excessive toxicity, irritation, allergic response, or other problem complications commensurate with a reasonable benefit/risk ratio.

As used herein, "dosage unit" refers to physically discrete units suited as unitary dosages for the particular individual to be treated. Each unit may contain a predetermined quantity of active compound(s) calculated to produce the desired therapeutic effect(s) in association with the required pharmaceutical carrier. The specification for the dosage unit forms of the invention may be dictated by (a) the unique characteristics of the active compound(s) and the particular therapeutic effect(s) to be achieved, and (b) the limitations inherent in the art of compounding such active compound(s).

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like. These physiologically acceptable salts are prepared by methods known in the art, e.g., by dissolving the free amine bases with an excess of the acid in aqueous alcohol, or neutralizing a free carboxylic acid with an alkali metal base such as a hydroxide, or with an amine.

Compounds described herein throughout, can be used or prepared in alternate forms. For example, many amino-containing compounds can be used or prepared as an acid addition salt. Often such salts improve isolation and handling properties of the compound. For example, depending on the reagents, reaction conditions and the like, compounds as described herein can be used or prepared, for example, as their hydrochloride or tosylate salts. Isomorphic crystalline forms, all chiral and racemic forms, N-oxide, hydrates, solvates, and acid salt hydrates, are also contemplated to be within the scope of the present invention.

As used herein, "patient" refers to animals, including mammals, preferably humans.

As used herein, the term "stereoisomers" refers to compounds that have identical chemical constitution, but differ as regards the arrangement of the atoms or groups in space.

The terms "treatment" and "treating" as used herein include preventative (e.g., prophylactic), curative and/or palliative treatment.

As used herein, "N-oxide" refers to compounds wherein the basic nitrogen atom of either a heteroaryl ring or tertiary amine is oxidized to give a quaternary nitrogen bearing a positive formal charge and an attached oxygen atom bearing a negative formal charge. When any variable occurs more than one time in any constituent or in any formula, its definition in each occurrence is independent of its definition at every other occurrence. Combinations of substituents and/or variables are permissible only if such combinations result in stable compounds.

As used herein, "hydrate" refers to a compound of the present invention which is associated with water in the molecular form, i.e., in which the H—OH bond is not split, and may be represented, for example, by the formula $R.H_2O$, where R is a compound of the invention. A given compound may form more than one hydrate including, for example, monohydrates ($R.H_2O$) or polyhydrates ($R.nH_2O$ wherein n is an integer >1) including, for example, dihydrates ($R.2H_2O$), trihydrates ($R.3H_2O$), and the like, or hemihydrates, such as, for example, $R.n_{1/2}H_2O$, $R.n_{1/3}H_2O$, $R.n_{1/4}H_2O$ and the like wherein n is an integer.

As used herein, "solvate" refers to a compound of the present invention which is associated with solvent in the molecular form, i.e., in which the solvent is coordinatively bound, and may be represented, for example, by the formula R.(solvent), where R is a compound of the invention. A given compound may form more than one solvate including, for example, monosolvates (R.(solvent)) or polysolvates (R.n (solvent)) wherein n is an integer >1) including, for example, disolvates (R.2(solvent)), trisolvates (R.3(solvent)), and the like, or hemisolvates, such as, for example, $R.n_{1/2}$(solvent), $R.n_{1/3}$(solvent), $R.n_{1/4}$(solvent) and the like wherein n is an integer. Solvents herein include mixed solvents, for example, methanol/water, and as such, the solvates may incorporate one or more solvents within the solvate.

As used herein, "acid hydrate" refers to a complex that may be formed through association of a compound having one or more base moieties with at least one compound having one or more acid moieties or through association of a compound having one or more acid moieties with at least one compound having one or more base moieties, said complex being further associated with water molecules so as to form a hydrate, wherein said hydrate is as previously defined and R represents the complex herein described above.

In any of the above teachings, a compound of the invention may be either a compound of one of the formulae herein described, or a stereoisomer, prodrug, pharmaceutically acceptable salt, hydrate, solvate, acid salt hydrate, N-oxide or isomorphic crystalline form thereof.

"Stable compound" and "stable structure" are meant to indicate a compound that is sufficiently robust to survive isolation to a useful degree of purity from a reaction mixture, and formulation into an efficacious therapeutic agent. Stable compounds are preferred in accordance with the present invention.

It is believed the chemical formulas and names used herein correctly and accurately reflect the underlying chemical compounds. However, the nature and value of the present invention does not depend upon the theoretical correctness of these formulae, in whole or in part. Thus it is understood that the formulas used herein, as well as the chemical names attributed to the correspondingly indicated compounds, are not intended to limit the invention in any way, including restricting it to any specific tautomeric form or to any specific optical or geometric isomer, except where such stereochemistry is clearly defined.

As used herein, "prodrug" refers to compounds specifically designed to maximize the amount of active species that reaches the desired site of reaction, which are of themselves typically inactive or minimally active for the activity desired, but through biotransformation are converted into biologically active metabolites. The present invention contemplates the compounds disclosed herein to be used as prodrugs. The term "prodrug" is intended to include any molecule that is transformed into a compound according to formula (I) or any other compound of the present invention in vivo following administration to a mammal. A prodrug form of a compound of the present invention, such as a compound of formula I, can be prepared, for example, by modifying functional groups present in the compound in such a way that the modifications are cleaved, either in routine manipulation or in vivo, to the parent compound. Prodrugs include compounds of the present invention wherein the hydroxy or amino group is bonded to any group that, when the prodrug is administered to a mammal subject, cleaves to form a free hydroxyl or free amino, respectively. Examples include, but are not limited to, acetate, formate and benzoate derivatives of alcohol and amine functional groups; and alkyl, cycloalkyl, aryl, and alkylaryl esters such as methyl, ethyl, propyl, isopropyl, butyl, isobutyl, sec-butyl, tert-butyl, cyclopropyl, phenyl, benzyl, and phenethyl esters, and the like. The compounds employed in the methods and compositions of the present invention may exist in prodrug form. Since prodrugs are known to enhance numerous desirable qualities of pharmaceuticals (e.g., solubility, bioavailability, manufacturing, etc.), the compounds described herein may, if desired, be delivered in prodrug form. Thus, the present invention contemplates compositions and methods involving prodrugs.

Compounds described herein may contain one or more asymmetrically substituted carbon atoms, and may be isolated in optically active or racemic forms. Thus, all isomeric forms of a structure, including all stereogenic (such as enantiomeric, diastereomeric, and/or meso forms, whether chiral or racemic), all achiral, all geometric, and/or all conformational isomeric forms are intended, unless the specific stereochemical or other isomeric form is specifically indicated and/or achiral. It is well known in the art how to prepare and isolate such isomeric forms of a structure including those having stereogenic centers including those stereogenic forms wherein the structure is present in optically active form. For example, mixtures of stereoisomers may be separated by standard techniques including, but not limited to, resolution of racemic forms, normal, reverse-phase, and chiral chromatography, preferential salt formation, recrystallization, and the like, or by chiral synthesis either from chiral starting materials or by deliberate synthesis of target chiral centers.

Accordingly, in certain embodiments, the present invention is directed, in part, to novel compounds of formula I or Ia:

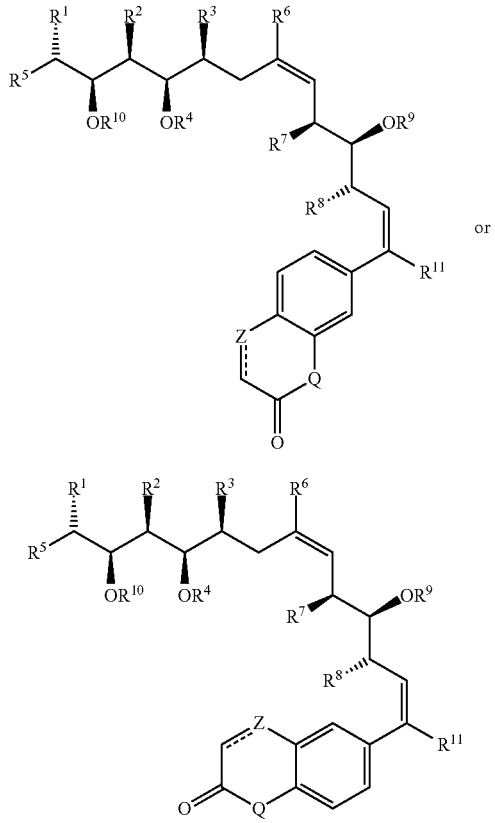

wherein:
- ---- represents the presence of a single bond or double bond;
- $R^1$, $R^2$, $R^3$, $R^6$, $R^7$, $R^8$, and $R^{11}$ are each independently H or $C_{1-10}$alkyl;
- $R^4$ and $R^9$ are each independently H or acid labile protecting group;
- $R^5$ is $C_{2-6}$monoalkenyl or $C_{4-6}$alkadienyl;
- $R^{10}$ is H, —C(=O)$NR^{13}R^{14}$, or oxidatively labile hydroxyl protecting group;
- Q is —O— or —$NR^{12}$;
- Z is —CH—, —$CH_2$—, or —O—, provided that when ---- represents a double bond, then Z is —CH—;
- $R^{12}$ is H, alkyl, or acid labile amino protecting group;
- $R^{13}$ and $R^{14}$ are each independently H, $C_{1-10}$alkyl, $C_{2-6}$alkenyl, $C_{2-6}$alkynyl, $OR^c$, C(=O)$R^b$, S(O)$_pR^b$, $(CH_2)_r$$C_{3-12}$carbocycle, or $(CH_2)_r$heterocycle having 5 to 12 ring atoms; or $R^{13}$ and $R^{14}$ taken together with the nitrogen atom to which they are attached form a 5- or 6-membered heterocycle containing 0-3 additional heteroatoms selected from O, S, and N;
- $R^b$ and $R^c$ are each independently H, $C_{1-6}$alkyl, $C_{2-6}$alkenyl, $C_{2-6}$alkynyl, $C_{3-6}$cycloalkyl, or $(CH_2)_r$phenyl;
- p is 1 or 2; and
- each r is independently 0, 1, 2, 3, or 4;

or a pharmaceutically acceptable salt thereof.

In certain preferred embodiments, the compounds of the invention is directed to compounds of formula I above, or a pharmaceutically acceptable salt thereof.

In formula I or Ia above, $R^1$, $R^2$, $R^3$, $R^6$, $R^7$, $R^8$, and $R^{11}$ are each independently H or $C_{1-10}$alkyl. In certain preferred embodiments, $R^1$, $R^2$, $R^3$, $R^6$, $R^7$, $R^8$, and $R^{11}$ are each independently H or $C_{1-3}$alkyl, more preferably H or methyl, with each as methyl being even more preferred.

In the above formula I, $R^4$ and $R^9$ are each independently H or an acid labile protecting group, more preferably H.

In formula I or Ia above, $R^5$ is $C_{2-6}$monoalkenyl or $C_{4-6}$alkadienyl, preferably $C_{2-6}$ monoalkenyl. In certain preferred embodiments where $R^5$ is $C_{2-6}$monoalkenyl, it is preferably $C_{2-4}$monoalkenyl, with

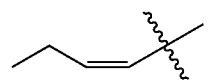

being even more preferred. In preferred embodiments where $R^5$ is $C_{4-6}$alkadienyl, it is more preferably 1,3-butadien-1-yl.

In certain embodiments of formula I or Ia compounds above, $R^{10}$ is H, —C(=O)$NR^{13}R^{14}$, or oxidatively labile hydroxyl protecting group; preferably $R^{10}$ is H or —C(=O)$NR^{13}R^{14}$, with H being even more preferred.

In other embodiments of compounds of formula I or Ia above, Q is —O— or —$NR^{12}$, more preferably —O—.

In certain formula I or Ia compounds, Z is —CH—, —$CH_2$—, or —O—, provided that when ---- represents a double bond, then Z is —CH—. Preferably Z is —CH—, —$CH_2$—, with —CH—, being more preferred.

In formula I or Ia compounds above, $R^{12}$ is H, alkyl, or acid labile amino protecting group. In certain preferred embodiments, $R^{12}$ is H or alkyl, more preferably H. In other preferred embodiments, $R^{12}$ is H or acid labile amino protecting group, more preferably H.

In the above f formula I or Ia compounds, ---- represents the presence of a single bond or double bond. In certain preferred embodiments, ---- represents the presence of a single bond. In other more ---- represents the presence of a double bond.

In certain embodiments of formula I or Ia compounds, $R^{13}$ and $R^{14}$ are each independently H, $C_{1-10}$alkyl, $C_{2-6}$alkenyl, $C_{2-6}$alkynyl, $OR^c$, C(=O)$R^b$, S(O)$_pR^b$, $(CH_2)_r$$C_{3-12}$carbocycle, or $(CH_2)_r$heterocycle having 5 to 12 ring atoms; preferably H, $C_{1-10}$alkyl, $(CH_2)_r$ $C_{3-12}$carbocycle, or $(CH_2)_r$heterocycle having 5 to 12 ring atoms; with at least one of $R^{13}$ and $R^{14}$ being H more preferred. Most preferably, both are H.

In certain other embodiments of formula I compounds, $R^{13}$ and $R^{14}$ taken together with the nitrogen atom to which they are attached form a 5- or 6-membered heterocycle containing 0-3 additional heteroatoms selected from O, S, and N.

In some embodiments of formula I or Ia compounds, $R^b$ and $R^c$ are each independently H, $C_{1-6}$alkyl, $C_{2-6}$alkenyl, $C_{2-6}$alkynyl, $C_{3-6}$cycloalkyl, or $(CH_2)_r$phenyl; preferably H, $C_{1-6}$alkyl, $C_{3-6}$cycloalkyl, or $(CH_2)_r$phenyl; still more preferably H or $C_{1-6}$alkyl.

In the above formula I or Ia compounds, each r is independently 0, 1, 2, 3, or 4; preferably 0, 1, or 2; more preferably 0 or 1.

In certain embodiments the compound of formula I has the structure:

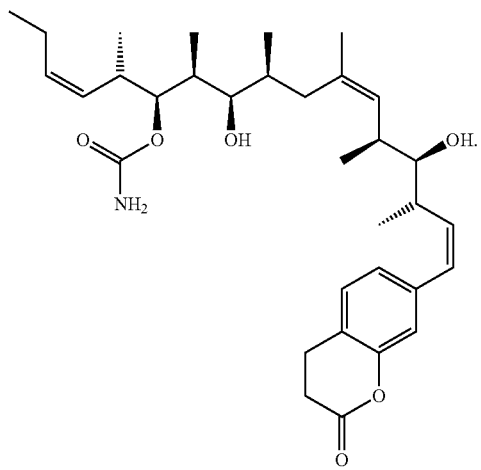

In certain other embodiments the compound of formula I has the structure:

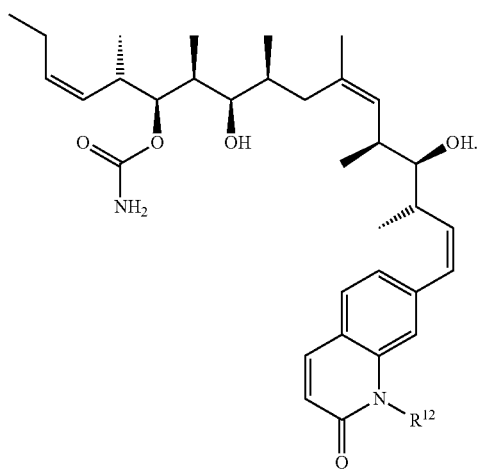

In some embodiments the compound of formula I has the structure:

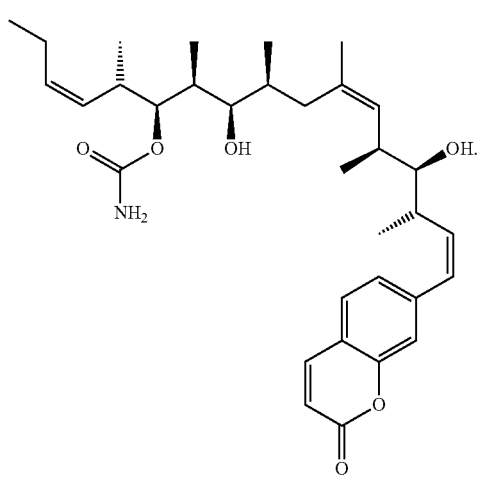

In other embodiments the compound of formula I has the structure:

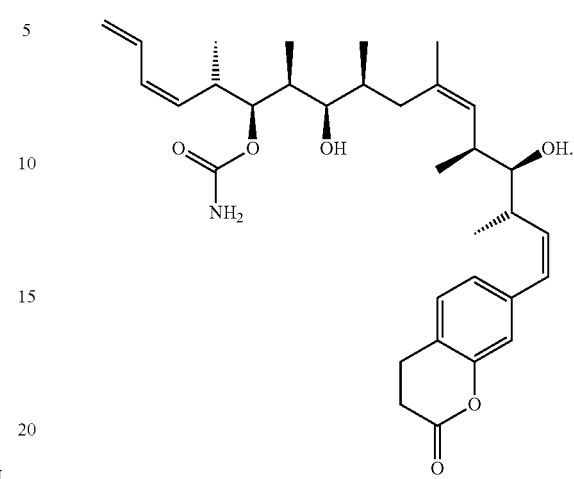

In still other embodiments, the compound of formula I has the structure:

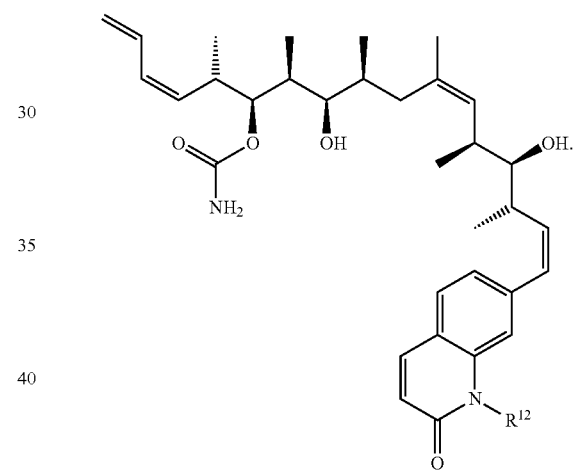

In other embodiments the compound of formula I has the structure:

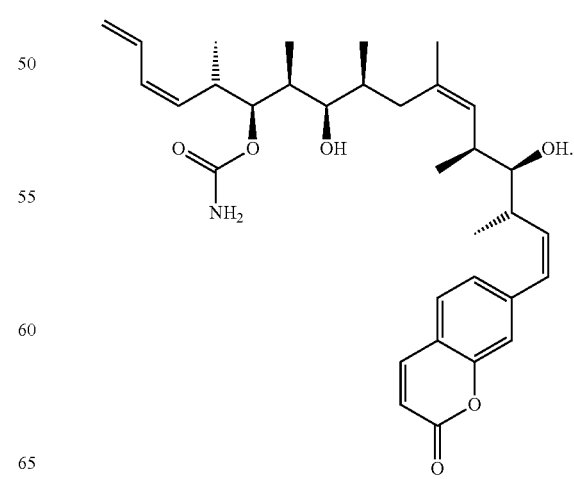

In other embodiments the compound of formula Ia has the structure:

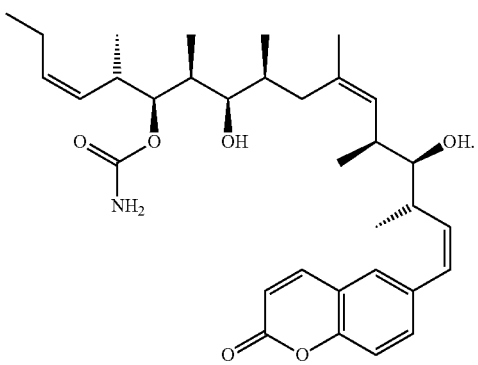

In other embodiments the compound of formula I has the structure:

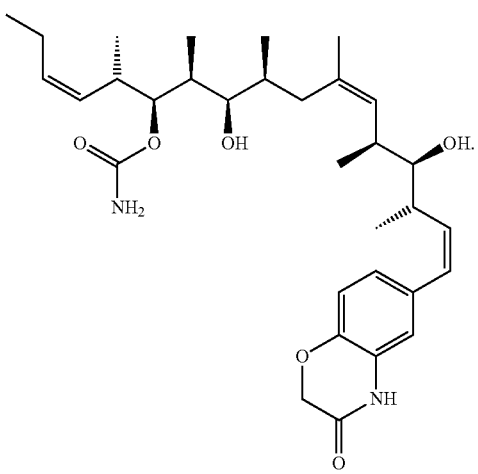

In other embodiments the compound of formula I has the structure:

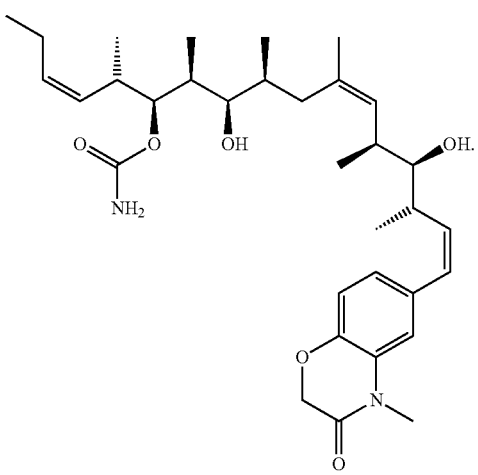

In other embodiments the compound of formula I has the structure:

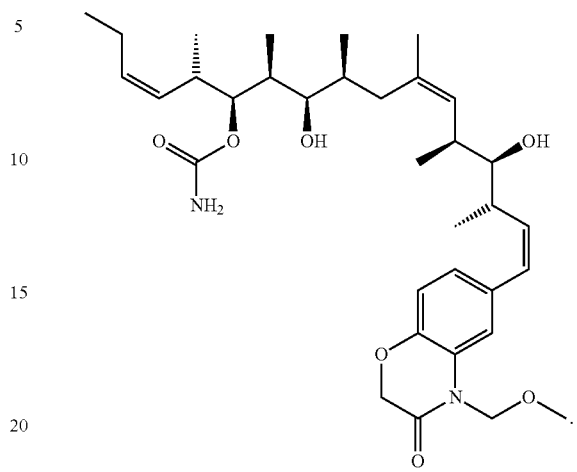

In any of the above embodiments of compounds of formula I or Ia the compound may be present as its pharmaceutically acceptable salt (including all combinations and subcombinations of compounds of formula I or Ia).

The compounds of the present invention may be prepared in a number of ways well known to those skilled in the art. The compounds can be synthesized, for example, by the methods described below, or variations thereon as appreciated by the skilled artisan. All processes disclosed in association with the present invention are contemplated to be practiced on any scale, including milligram, gram, multigram, kilogram, multikilogram or commercial industrial scale.

The microtubule stabilizing compounds of the present invention, such as compounds of formula I or Ia, may be administered by any means that results in the contact of the active agent with the agent's site of action in the body of a patient. The compounds may be administered by any conventional means available for use in conjunction with pharmaceuticals, either as individual therapeutic agents or in a combination of therapeutic and/or prophylactic agents. For example, they may be administered as the sole active agent in a pharmaceutical composition, or they can be used in combination with other therapeutically active ingredients including, for example, anti-cancer compounds, such as cis-platin, paclitaxel, or epithilones, or analgesics for the treatment of pain associated with cancer or its treatment, such as for example, opioid analgesic agents or cannabinoid receptor modulators. In such combinations, selected compounds of the invention may provide equivalent or even enhanced therapeutic activity such as, for example, pain ameliorization, while providing reduced adverse side effects associated with opioids, such as addiction or pruritus, by lowering the amount of opioid required to achieve a therapeutic effect.

Generally, therapeutic compounds of this invention may be administered to a patient alone or in combination with a pharmaceutically acceptable carrier or diluent. Accordingly, the compounds of the invention, for example, compounds of formula I or Ia, are preferably combined with a pharmaceutical carrier selected on the basis of the chosen route of administration and standard pharmaceutical practice as described, for example, in *Remington's Pharmaceutical Sciences* (Mack Publishing Co., Easton, Pa., 1980), the disclosures of which are hereby incorporated herein by reference, in their entireties. The carrier(s) must be acceptable in the sense of being compatible with the other ingredients of the composition and not deleterious to the recipient thereof.

In addition to the pharmaceutical carrier, the compound of the invention, for example, compounds of formula I or Ia, may be co-administered with at least one opioid, preferably a μ opioid receptor modulator compound. The utility of such combination products may be determined by those skilled in the art using established animal models. Suitable opioids include, without limitation, alfentanil, allylprodine, alphaprodine, anileridine, benzyl-morphine, bezitramide, buprenorphine, butorphanol, clonitazene, codeine, cyclazocine, desomorphine, dextromoramide, dezocine, diampromide, diamorphone, dihydrocodeine, dihydromorphine, dimenoxadol, dimepheptanol, dimethylthiambutene, dioaphetylbutyrate, dipipanone, eptazocine, ethoheptazine, ethylmethylthiambutene, ethylmorphine, etonitazene, fentanyl, heroin, hydrocodone, hydromorphone, hydroxypethidine, isomethadone, ketobemidone, levallorphan, levorphanol, levophenacylmorphan, lofentanil, loperamide, meperidine (pethidine), meptazinol, metazocine, methadone, metopon, morphine, myrophine, nalbuphine, narceine, nicomorphine, norlevorphanol, normethadone, nalorphine, normorphine, norpinanone, opium, oxycodone, oxymorphone, papaveretum, pentazocine, phenadoxone, phenomorphan, phanazocine, phenoperidine, piminodine, piritramide, propheptazine, promedol, properidine, propiram, propoxyphene, sulfentanil, tilidine, tramadol, diastereoisomers thereof, pharmaceutically acceptable salts thereof, complexes thereof; and mixtures thereof.

Other opioids, optional conventional opioid components, and optional compounds for enhancing the analgesic potency of the opioid and/or for reducing analgesic tolerance development, that may be employed in the methods and compositions of the present invention, in addition to those exemplified above, would be readily apparent to one of ordinary skill in the art, once armed with the teachings of the present disclosure.

Compounds of the present invention can be administered to a mammalian host in a variety of forms adapted to the chosen route of administration, e.g., orally or parenterally. Parenteral administration in this respect includes administration by the following routes: intravenous, intramuscular, subcutaneous, rectal, intraocular, intrasynovial, transepithelial including transdermal, ophthalmic, sublingual and buccal; topically including ophthalmic, dermal, ocular, rectal, and nasal inhalation via insufflation aerosol.

The active compound may be orally administered, for example, with an inert diluent or with an assimilable edible carrier, or it may be enclosed in hard or soft shell gelatin capsules, or it may be compressed into tablets, or it may be incorporated directly with the food of the diet. For oral therapeutic administration, the active compound may be incorporated with excipient and used in the form of ingestible tablets, buccal tablets, troches, capsules, elixirs, suspensions, syrups, wafers, and the like. Such compositions and preparations should preferably contain at least 0.1% of active compound. The percentage concentration of active compound in the compositions and preparations may, of course, be varied, and the relative proportions of active ingredient and carrier may be determined, for example, by the solubility and chemical nature of the compound, chosen route of administration and standard pharmaceutical practice. Generally speaking, the concentration of active agent may be, for example, from about 2 to about 6% of the weight of the unit. The amount of active compound in such therapeutically useful compositions is preferably such that a suitable dosage will be obtained. Preferred compositions or preparations according to the present invention may be prepared so that an oral dosage unit form contains from about 0.1 to about 1000 mg of active compound (and all combinations and subcombinations of dosage ranges and specific dosage amounts therein).

The tablets, troches, pills, capsules and the like may also contain one or more of the following: a binder, such as gum tragacanth, acacia, corn starch or gelatin; an excipient, such as dicalcium phosphate; a disintegrating agent, such as corn starch, potato starch, alginic acid and the like; a lubricant, such as magnesium stearate; a sweetening agent such as sucrose, lactose or saccharin; or a flavoring agent, such as peppermint, oil of wintergreen or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavoring, such as cherry or orange flavor. Of course, any material used in preparing any dosage unit form is preferably pharmaceutically pure and substantially non-toxic in the amounts employed. In addition, the active compound may be incorporated into sustained-release preparations and formulations.

The active compound may also be administered parenterally or intraperitoneally. Solutions of the active compound as a free base or a pharmacologically acceptable salt can be prepared in water suitably mixed with a surfactant, such as hydroxypropylcellulose. A dispersion can also be prepared in glycerol, liquid polyethylene glycols and mixtures thereof and in oils. Under ordinary conditions of storage and use, these preparations may contain a preservative to prevent the growth of microorganisms.

The pharmaceutical forms suitable for injectable use include, for example, sterile aqueous solutions or dispersions and sterile powders for the extemporaneous preparation of sterile injectable solutions or dispersions. In all cases, the form is preferably sterile and fluid to provide easy syringability. It is preferably stable under the conditions of manufacture and storage and is preferably preserved against the contaminating action of microorganisms such as bacteria and fungi. The carrier may be a solvent or dispersion medium containing, for example, water, ethanol, polyol (for example, glycerol, propylene glycol, liquid polyethylene glycol and the like), suitable mixtures thereof, and vegetable oils. The proper fluidity can be maintained, for example, by the use of a coating, such as lecithin, by the maintenance of the required particle size in the case of a dispersion, and by the use of surfactants. The prevention of the action of microorganisms may be achieved by various antibacterial and antifungal agents, for example, parabens, chlorobutanol, phenol, sorbic acid, thimerosal and the like. In many cases, it will be preferable to include isotonic agents, for example, sugars or sodium chloride. Prolonged absorption of the injectable compositions may be achieved by the use of agents delaying absorption, for example, aluminum monostearate and gelatin.

Sterile injectable solutions may be prepared by incorporating the active compound in the required amount, in the appropriate solvent, with various of the other ingredients enumerated above, as required, followed by filtered sterilization. Generally, dispersions may be prepared by incorporating the sterilized active ingredient into a sterile vehicle that contains the basic dispersion medium and the required other ingredients from those enumerated above. In the case of sterile powders for the preparation of sterile injectable solutions, the preferred methods of preparation may include vacuum drying and the freeze-drying technique that yield a powder of the active ingredient, plus any additional desired ingredient from the previously sterile-filtered solution thereof.

The dosage of the compounds of the present invention that will be most suitable for prophylaxis or treatment will vary with the form of administration, the particular compound chosen and the physiological characteristics of the particular patient under treatment. Generally, small dosages may be used initially and, if necessary, increased by small increments until the desired effect under the circumstances is reached. The therapeutic human dosage, based on physiological studies using rats, may generally range from about 100 mg to about 1.5 grams per day, and all combinations and subcombinations of ranges and specific dosages therein. Alternatively, the therapeutic human dosage may be from about 0.4 mg to about 10 g or higher, and may be administered in several different dosage units from once to several times a day. Generally speaking, oral administration may require higher dosages.

It will be further appreciated that the amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

Combination products of this invention, such as pharmaceutical compositions comprising the compounds of the present invention, for example, compounds of formula I, in combination with other therapeutic compounds described herein may be in any dosage form, such as those described herein, and can also be administered in various ways, as described herein. In a preferred embodiment, the combination products of the invention are formulated together, in a single dosage form (that is, combined together in one capsule, tablet, powder, or liquid, etc.). When the combination products are not formulated together in a single dosage form, the compounds of the present invention and other therapeutic compounds described herein may be administered at the same time (that is, together), or in any order. When not administered at the same time, preferably the administration of a compound of the invention and other therapeutic compounds as described herein occurs less than about one hour apart, more preferably less than about 30 minutes apart, even more preferably less than about 15 minutes apart, and still more preferably less than about 5 minutes apart. Preferably, administration of the combination products of the invention is oral, although other routes of administration, as described above, are contemplated to be within the scope of the present invention. Although it is preferable that the compound of the invention and other therapeutic compounds as described herein are both administered in the same fashion (that is, for example, both orally), if desired, they may each be administered in different fashions (that is, for example, one component of the combination product may be administered orally, and another component may be administered intravenously). The dosage of the combination products of the invention may vary depending upon various factors such as the pharmacodynamic characteristics of the particular agent and its mode and route of administration, the age, health and weight of the recipient, the nature and extent of the symptoms, the kind of concurrent treatment, the frequency of treatment, and the effect desired.

Although the proper dosage of the combination products of this invention will be readily ascertainable by one skilled in the art, once armed with the present disclosure, by way of general guidance, where one or more compounds of the present invention is combined with one or more other therapeutic compounds as described herein, for example, typically a daily dosage may range from about 20 to about 1500 milligrams of the compound of the invention (and all combinations and subcombinations of ranges therein) and about 20 to about 1500 milligrams of other therapeutic compounds as described herein (and all combinations and subcombinations of ranges therein), per day. Preferably, a daily dosage may be about 20 to about 1000 milligrams of the compound of the invention and about 20 to about 1000 milligrams of other therapeutic compounds as described herein per day. Even more preferably, the daily dosage may be about 40 to 200 milligrams of the compound of the invention and about 40 to 200 milligrams of other therapeutic compounds as described herein per day. With regard to a typical dosage form of this type of combination product, such as a tablet, the compound of the invention generally may be present in an amount of about 20 to about 1500 milligrams, and the other therapeutic compounds as described herein in an amount of about 0.2 to about 25 milligrams. In certain embodiments, the dosage is from about 1 to about 40 mg/m$^2$ of patient surface area and all combinations and subcombinations thereof, more preferably about 5 to about 20.

Particularly when provided as a single dosage form, the potential exists for a chemical interaction between the combined active ingredients (for example, a compound of the invention and other therapeutic compounds as described herein). For this reason, the preferred dosage forms of the combination products of this invention are formulated such that although the active ingredients are combined in a single dosage form, the physical contact between the active ingredients is minimized (that is, reduced).

In order to minimize contact, one embodiment of this invention where the product is orally administered provides for a combination product wherein one active ingredient is enteric coated. By enteric coating one or more of the active ingredients, it is possible not only to minimize the contact between the combined active ingredients, but also, it is possible to control the release of one of these components in the gastrointestinal tract such that one of these components is not released in the stomach but rather is released in the intestines. Another embodiment of this invention where oral administration is desired provides for a combination product wherein one of the active ingredients is coated with a sustained-release material that effects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a low-viscosity grade of hydroxypropyl methylcellulose (HPMC) or other appropriate materials as known in the art, in order to further separate the active components. The polymer coating serves to form an additional barrier to interaction with the other component.

Dosage forms of the combination products of the present invention wherein one active ingredient is enteric coated can be in the form of tablets such that the enteric coated component and the other active ingredient are blended together and then compressed into a tablet or such that the enteric coated component is compressed into one tablet layer and the other active ingredient is compressed into an additional layer. Optionally, in order to further separate the two layers, one or more placebo layers may be present such that the placebo layer is between the layers of active ingredients. In addition, dosage forms of the present invention can be in the form of capsules wherein one active ingredient is compressed into a tablet or in the form of a plurality of microtablets, particles, granules or non-perils, which are then enteric coated. These enteric coated microtablets, particles, granules or non-perils are then placed into a capsule or compressed into a capsule along with a granulation of the other active ingredient.

These as well as other ways of minimizing contact between the components of combination products of the present invention, whether administered in a single dosage form or administered in separate forms but at the same time by the same manner, will be readily apparent to those skilled in the art, once armed with the present disclosure.

The dose may also be provided by controlled release of the compound, by techniques well known to those in the art.

The present invention will now be illustrated by reference to the following specific, non-limiting examples. Those skilled in the art of organic synthesis may be aware of still other synthetic routes to the invention compounds. The reagents and intermediates used herein are commercially available or may be prepared according to standard literature procedures.

Methods of Preparation

7-Coumarincarboxaldehyde 3, available in one step from commercially available 7-methylcoumarin via selenium dioxide oxidation, was reacted directly with Wittig salt (+)-4 using the coupling tactic developed and refined in our laboratory (Scheme 1). (See (a) A. B. Smith, III, T. J. Beauchamp, T. J.; M. J. LaMarche, M. D. Kaufman, Y. Qui, H. Arimoto, D. R. Jones and K. Kobayashi, *J. Am. Chem. Soc.,* 2000, 122, 8654-8664; (b) A. B. Smith, III, B. S. Freeze, I. Brouard and T. Hirose, *Org. Lett.,* 2003, 5, 4405-4408). Coumarin 5 was obtained in 35%. Following union, standard conditions were then employed to generate coumarin (+)-6. Specifically, removal of the PMB ether permitted installation of the carbamate before global deprotection.

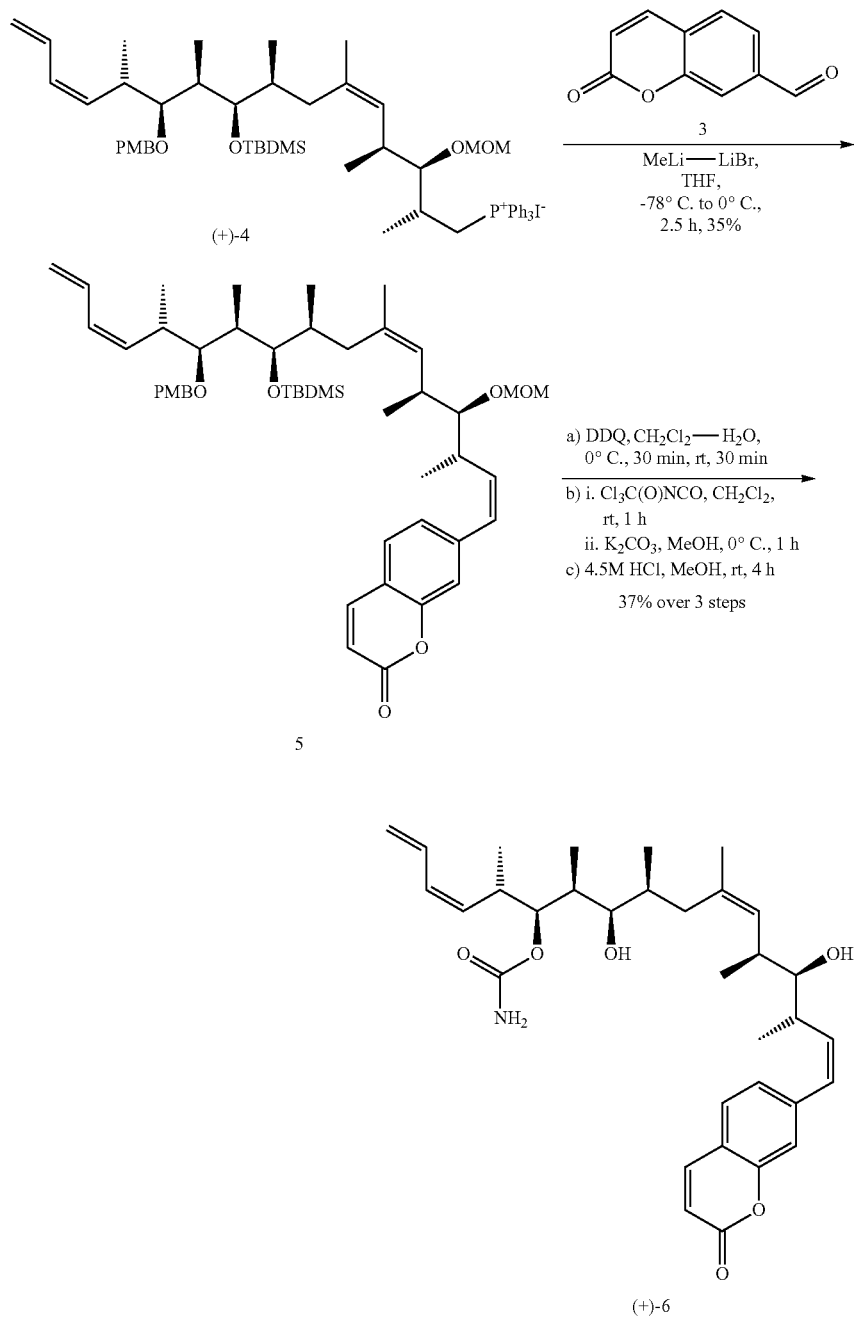

Scheme 1 Synthesis of the coumarin compound (+)-6

Union of the corresponding 23,24-dihydro Wittig salt (+)-7 (Scheme 2, see A. B. Smith, III and M. Xian, *Org. Lett.*, 2005, 7, 5229-5232) with coumarin aldehyde 3 proceeded smoothly. Further elaboratation led to the 23,24-dihydro analogue (+)-8, a compound that proved equivalent to (+)-1 and (+)-6 in the antiproliferative assays.

Scheme 2 Synthesis of the dihydrocoumarin compound (+)-8

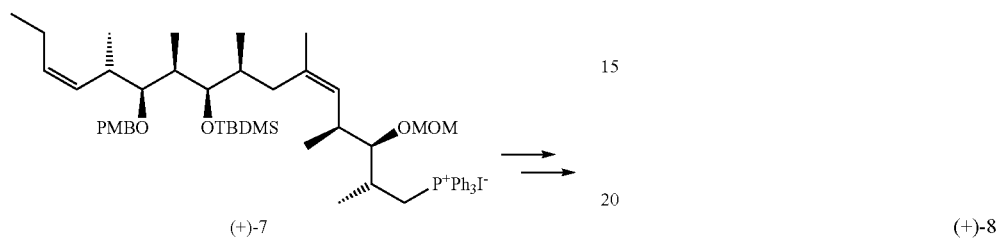

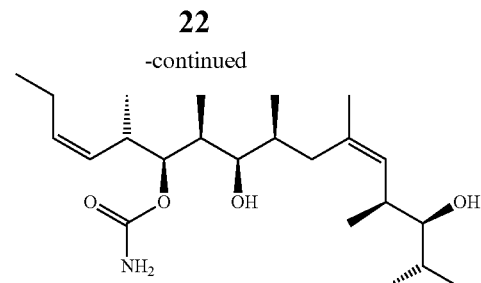

Scheme 3 Synthesis of the 6-coumarin analogue (+)-9

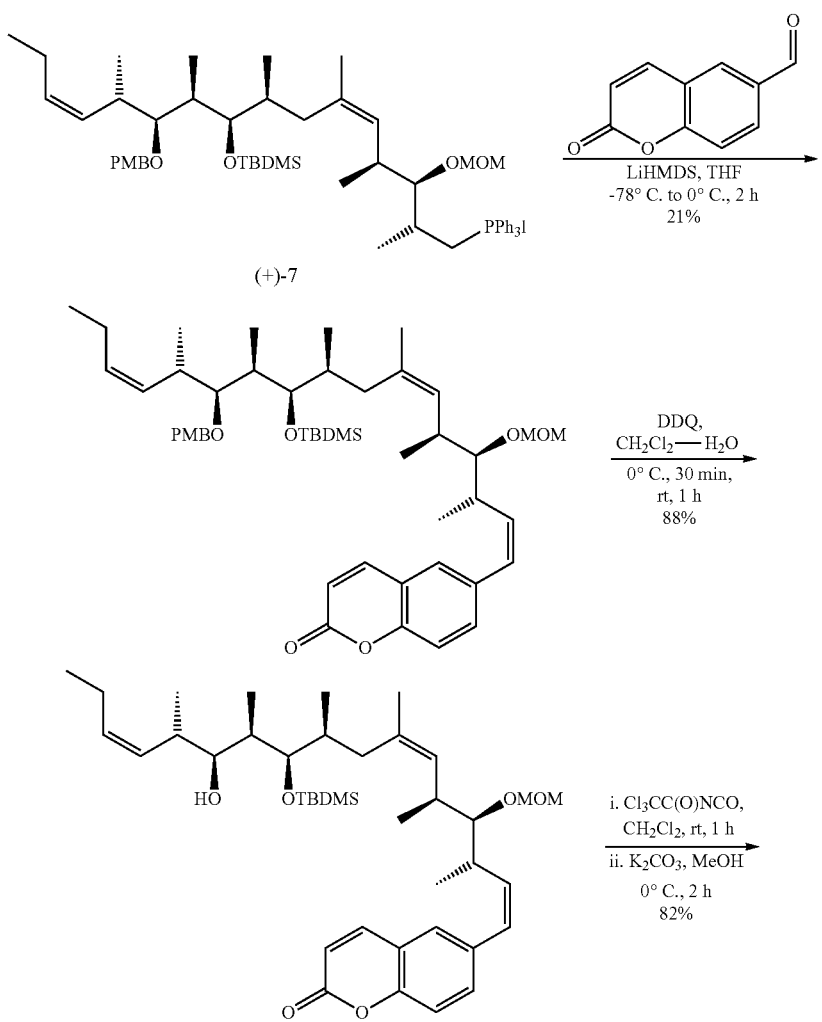

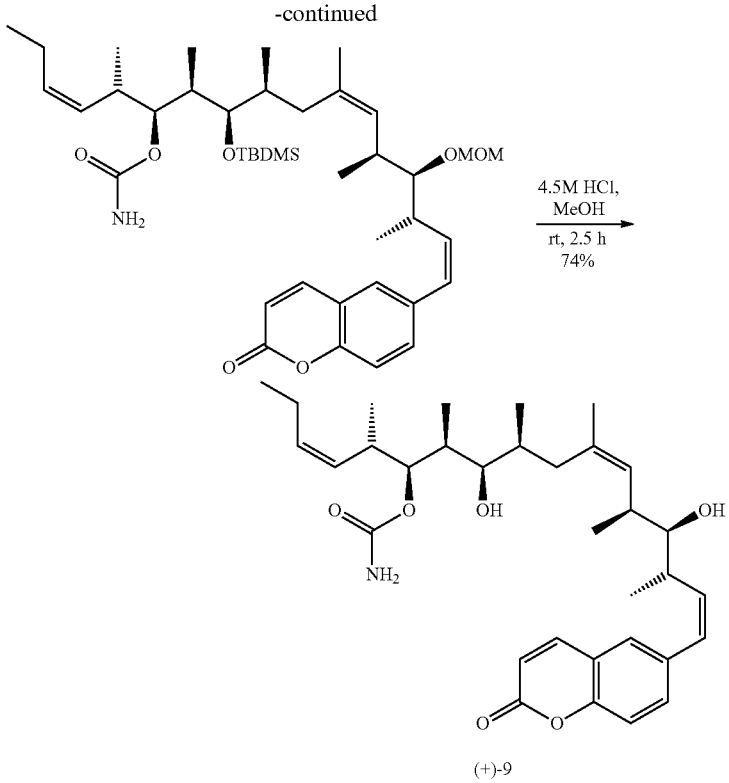

6-Coumarin analogue (+)-9 was prepared as shown in Scheme 3, substituting the 6 coumarin carboxaldehyde in place of the 7-isomer (depicted in Scheme 1 for compound 6.

Similarly, lactams 10, 11, and 12 were provided with appropriate substitution of the lactam aldehyde for the 7-coumarin carboxaldehyde as shown in Schemes 4, 5, and 6. The requisite unprotected lactam aldehyde proved readily accessible (T. R. Belliotti, D. J. Wustrow, W. D. Brink, K. T. Zoski, Y-H. Shih, S. Z. Whetzel, L. M. Georgic, A. E. Corbin, H. C. Akunne, T. G. Heffner, T. A. Pugsley and L. D. Wise, *J. Med. Chem.*, 1999, 42, 5181-5187).

Scheme 4 Protection of the lactam N-H of the coupling aldehyde

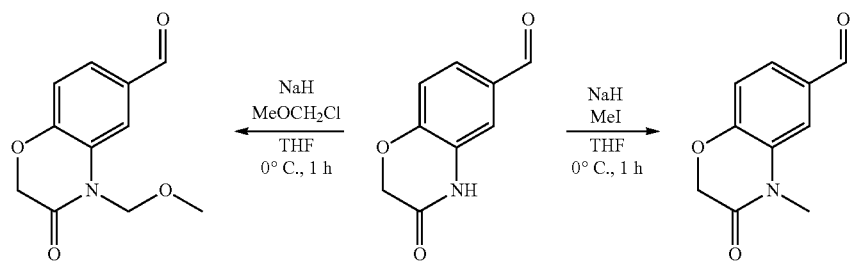

Scheme 5 Synthesis of the N-methyl lactam analogue (+)-11

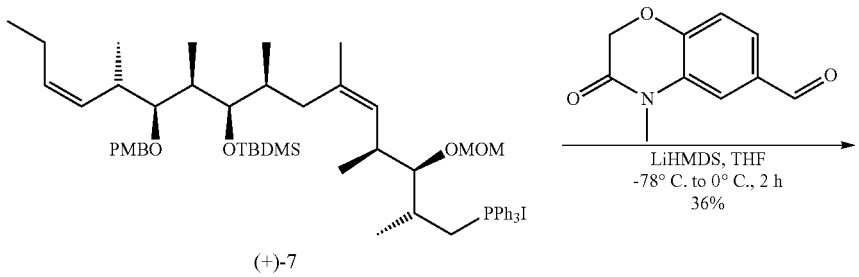

-continued
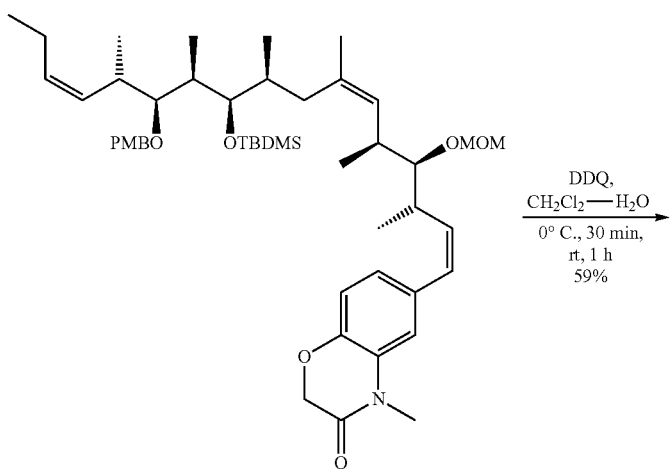
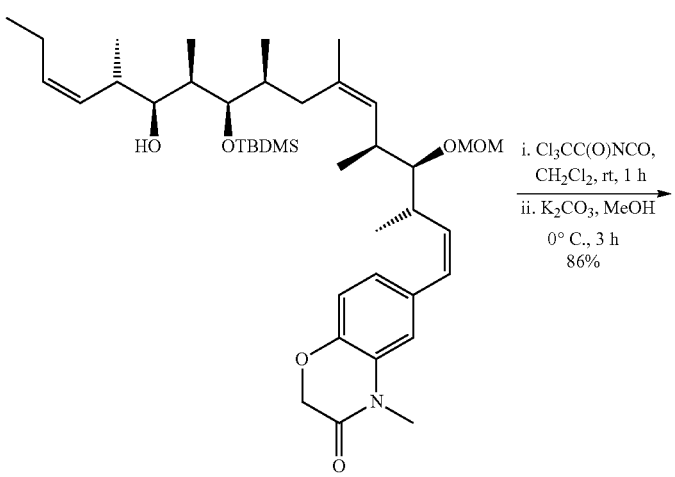
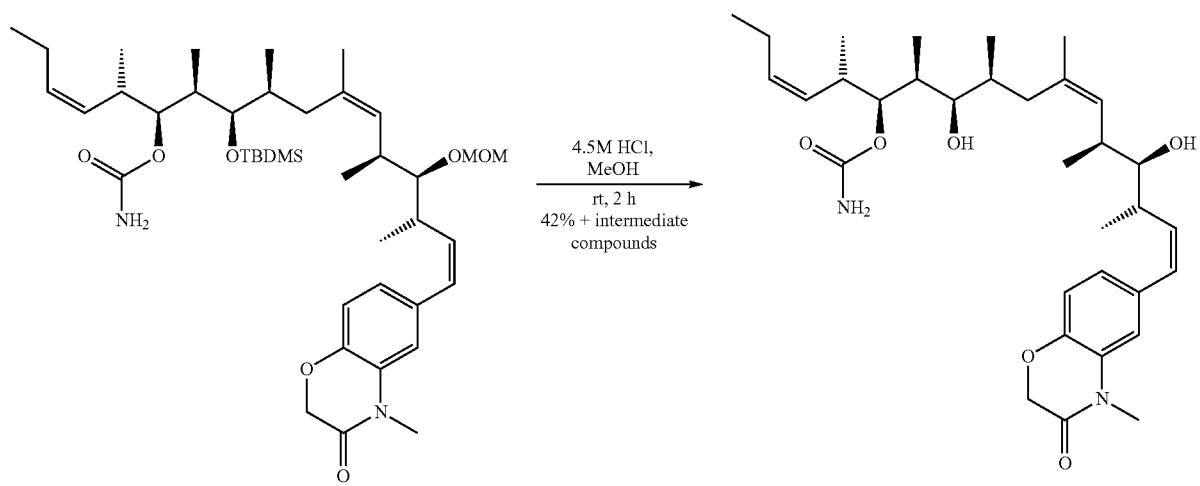
(+)-11

Scheme 6 Synthesis of the N-methoxymethyl lactam (+)-12 and the N-H lactam (-)-10 analogues
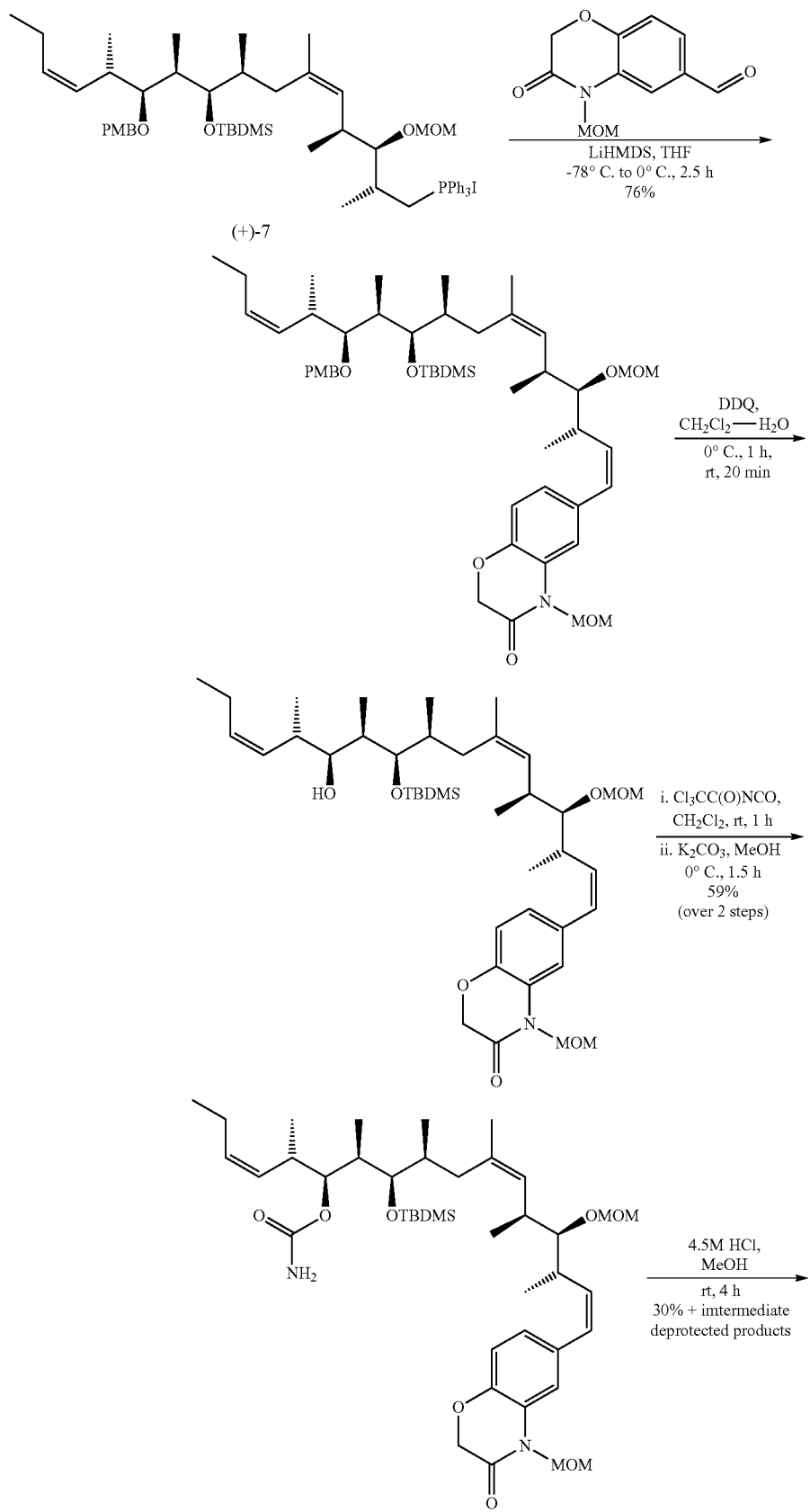

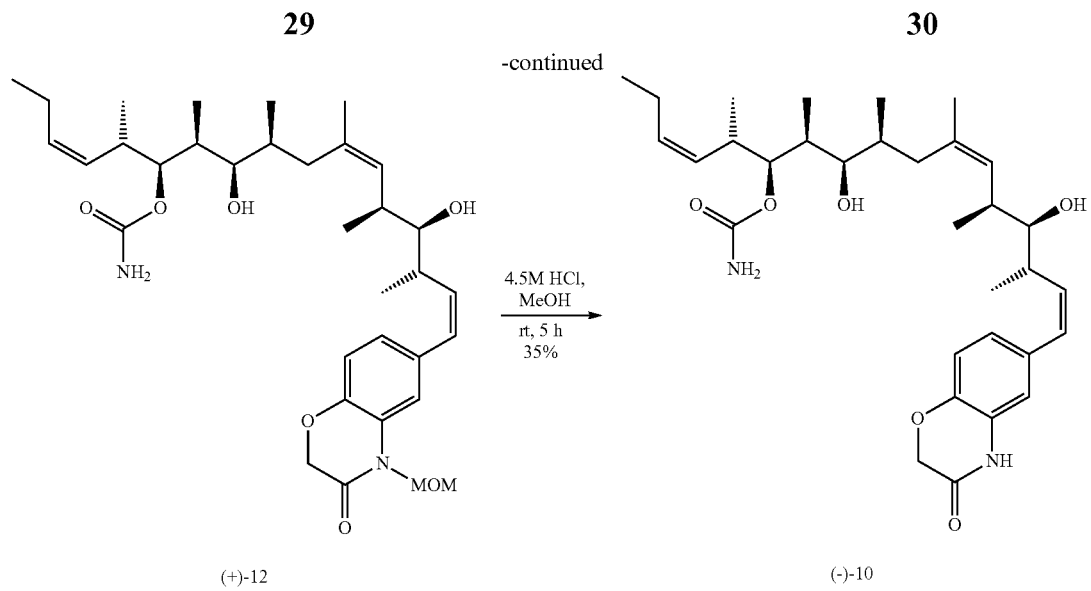

EXPERIMENTAL PROCEDURES

Example 1

Preparation of Coumarin Compound (+)-6

Coupling of the AB Diene to 7-Coumarin Carboxaldehyde

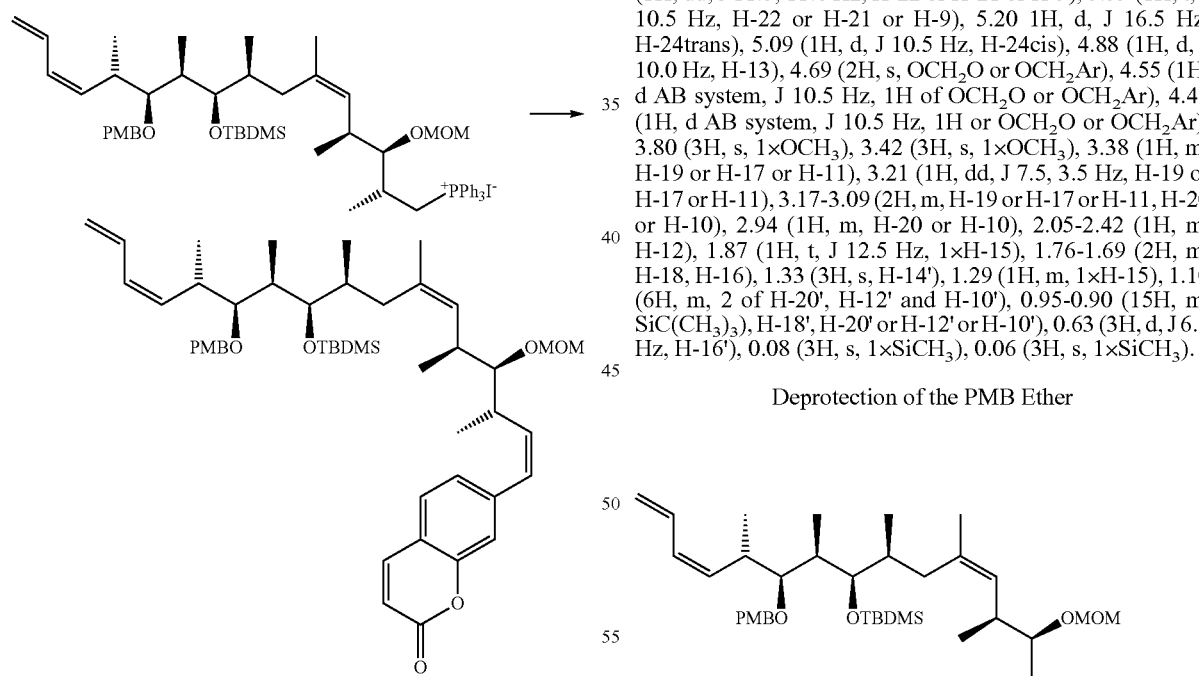

To a solution of azeotroped phosphonium salt (0.118 g, 0.116 mmol, 1.0 eq) in tetrahydrofuran (1.0 ml) at −78° C. was added methyllithium lithium iodide complex (0.14 ml of a 1.0M solution in tetrahydrofuran, 0.139 mmol, 1.2 eq). An orange-red solution resulted, which was stirred at −78° C. for 1 hour. A solution of azeotroped 7-coumarin carboxaldehyde (0.030 g, 0.174 mmol, 1.5 eq) in tetrahydrofuran (2.0 ml) precooled to −78° C. was added dropwise. The solution was stirred at −78° C. for 1 hour and warmed to −20° C. over 2 hours before adding $NH_4Cl$ (15 ml). The organics were extracted with EtOAc (3×15 ml), combined, washed with brine (20 ml), dried ($MgSO_4$) and concentrated under reduced pressure. Column chromatography (silica, 20% EtOAc-hexane) yielded the coupled compound (0.030 g, 35%) as a colourless oil; $^1H$ nmr (400 MHz, $CDCl_3$): δ 7.60 (1H, d, J 9.5 Hz, H-2), 7.36-7.26 (4H, m, 2H of ArH, H-6, H-7a or H-4a), 7.17 (1H, d, J 8.0 Hz, H-7a or H-4a), 6.87 (2H, d, J 8.5 Hz, 2H or ArH), 6.55 (1H, dt, J 17.0, 10.5 Hz, H-23), 6.39-6.34 (2H, H-8, H-3), 6.03 (1H, t, J 10.5 Hz, H-22 or H-21 or H-9), 5.87 (1H, dd, J 11.5, 11.0 Hz, H-22 or H-21 or H-9), 5.59 (1H, t, J 10.5 Hz, H-22 or H-21 or H-9), 5.20 1H, d, J 16.5 Hz, H-24trans), 5.09 (1H, d, J 10.5 Hz, H-24cis), 4.88 (1H, d, J 10.0 Hz, H-13), 4.69 (2H, s, $OCH_2O$ or $OCH_2Ar$), 4.55 (1H, d AB system, J 10.5 Hz, 1H of $OCH_2O$ or $OCH_2Ar$), 4.46 (1H, d AB system, J 10.5 Hz, 1H or $OCH_2O$ or $OCH_2Ar$), 3.80 (3H, s, 1×$OCH_3$), 3.42 (3H, s, 1×$OCH_3$), 3.38 (1H, m, H-19 or H-17 or H-11), 3.21 (1H, dd, J 7.5, 3.5 Hz, H-19 or H-17 or H-11), 3.17-3.09 (2H, m, H-19 or H-17 or H-11, H-20 or H-10), 2.94 (1H, m, H-20 or H-10), 2.05-2.42 (1H, m, H-12), 1.87 (1H, t, J 12.5 Hz, 1×H-15), 1.76-1.69 (2H, m, H-18, H-16), 1.33 (3H, s, H-14'), 1.29 (1H, m, 1×H-15), 1.10 (6H, m, 2 of H-20', H-12' and H-10'), 0.95-0.90 (15H, m, $SiC(CH_3)_3$), H-18', H-20' or H-12' or H-10'), 0.63 (3H, d, J 6.5 Hz, H-16'), 0.08 (3H, s, 1×$SiCH_3$), 0.06 (3H, s, 1×$SiCH_3$).

Deprotection of the PMB Ether

-continued

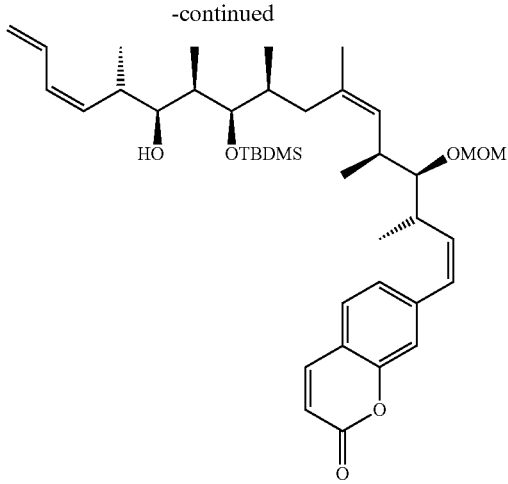

To a solution of the PMB ether (0.030 g, 0.041 mmol, 1.0 eq) in dichloromethane (1.0 ml) at 0° C. was added water (0.2 ml) followed by dichlorodicyanobenzoquinone (0.11 g, 0.049 mmol, 1.2 eq). The mixture was stirred at 0° C. for 15 minutes before adding NaHCO$_3$ (15 ml). The organics were extracted with CH$_2$Cl$_2$ (3×15 ml), combined, dried (MgSO$_4$) and concentrated under reduced pressure. The crude material was taken on without purification.

Formation of the Carbamate

To a solution of the crude alcohol (0.041 mmol, 1.0 eq) in dichloromethane (1.0 ml) was added trichloroacetylisocyanate (0.049 ml, 0.410 mmol, 10.0 eq). The solution was stirred at room temperature for 1 hour before concentrating under reduced pressure. The residue was cooled to 0° C., dissolved in methanol (1.0 ml) and freshly ground potassium carbonate added (0.100 g). The mixture was stirred at 0° C. for 1 hour and room temperature for 1.5 hours before adding water (15 ml). The organics was extracted with CH$_2$Cl$_2$ (4×15 ml), combined, dried (MgSO$_4$) and concentrated under reduced pressure. Column chromatography (silica, 30→50% EtOAc-hexane) yielded the carbamate (0.015 g, 56% over 2 steps) as a colourless oil; $^1$H nmr (400 MHz, CDCl$_3$): δ 7.68 (1H, d, J 9.5 Hz, H-2), 7.40 (1H, d, J 8.0 Hz, H-7a or H-4a), 7.24-7.21 (2H, m, H-6, H-7a or H-4a), 6.78 (1H, dt, J 17.0, 10.5 Hz, H-23), 6.37 (2H, m, H-8, H-3), 6.06 (1H, t, J 11.0 Hz, H-22), 5.89 (1H, dd, J 11.5, 11.0 Hz, H-9), 5.42 (1H, t, J 10.5 Hz, H-21), 5.23 (1H, d, J 16.5, H-24trans), 5.14 (1H, d, J 10.0 Hz, H-24cis), 4.82 (1H, d, J 10.5 Hz, H-13), 4.71-4.65 (5H, m, NH$_2$, OCH$_2$O, H-19), 3.43 (3H, s, OCH$_3$), 3.21 (1H, dd, J 4.5, 4.0 Hz, H-11), 3.17-3.13 (2H, m, H-11, H-10), 2.97 (1H, dt, J 10.0, 6.5 Hz, H-20), 2.40 (1H, m, H-12), 1.89 (1H, t, J 12.0 Hz, 1×H-15), 1.78 (1H, m, H-18), 1.61 (1H, m, H-16), 1.27 (1H, m, 1×H-15), 1.26 (3H, s, H-14'), 1.15 (3H, d, J 7.0 Hz, H-10'), 0.99 (3H, d, J 6.5 Hz, H-20'), 0.89 (12H, m, H-12', SiC(CH$_3$)$_3$), 0.81 (3H, d, J 7.0 Hz, H-18'), 0.62 (3H, d, J 7.0 Hz, H-16'), 0.10 (3H, s, 1×SiCH$_3$), 0.08 (3H, s, 1×SiCH$_3$).

Deprotection to Obtain the Discodermolide Coumarin Analogue (+)-6

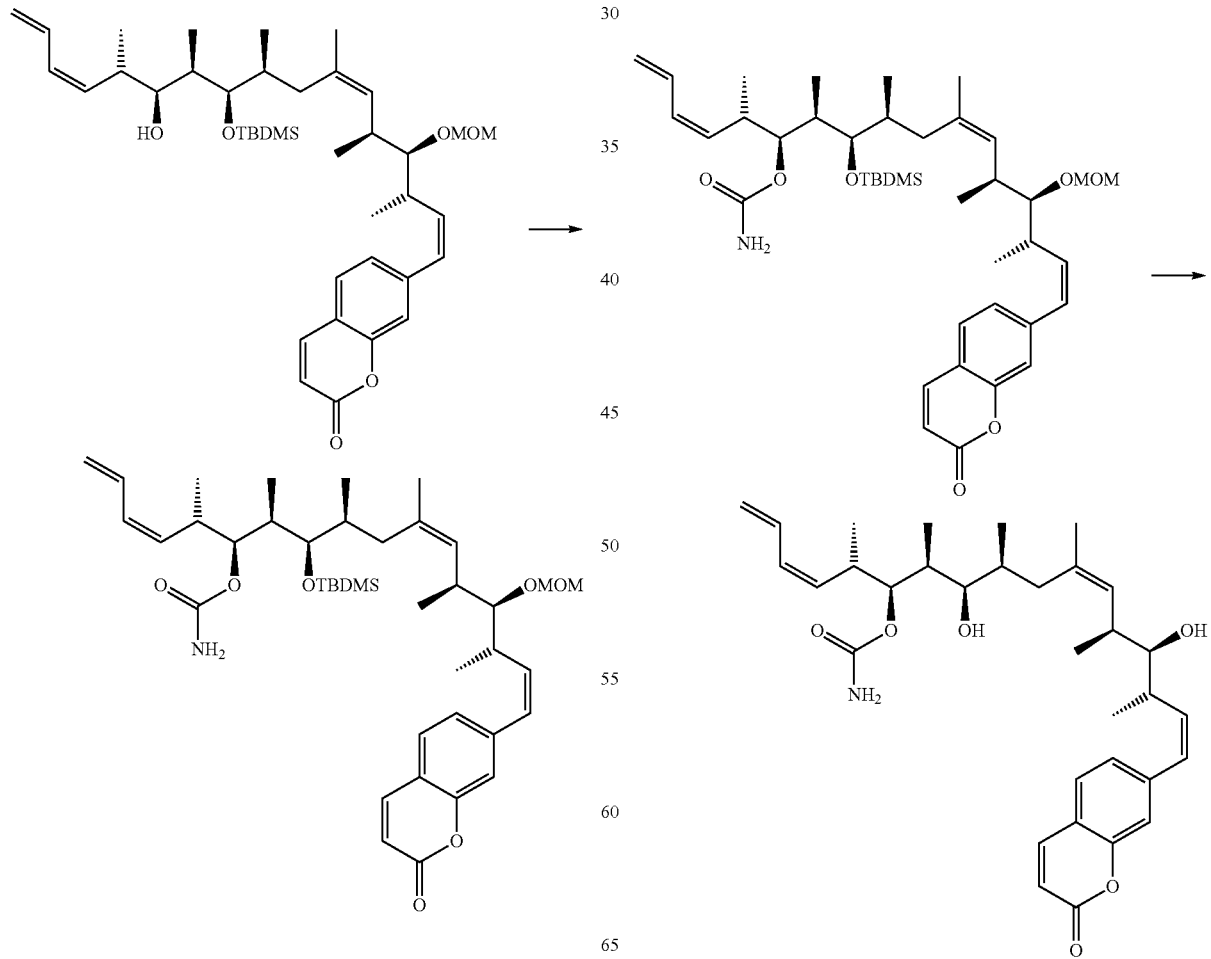

To a solution of the protected coumarin analogue (0.015 g, 0.023 mmol) in methanol (3.0 ml) was added hydrochloric acid (4.5M, 3×1.0 ml) in aliquots over 1 hour. The mixture was stirred at room temperature for 1 hour before adding further methanol (2.0 ml) and hydrochloric acid (4.5M, 1 ml). After an addition 1.5 hours at room temperature, the solution was neutralized with NaHCO$_3$ (20 ml) and the organics were extracted with CH$_2$Cl$_2$ (4×20 ml). The combined organics were dried (MgSO$_4$) and concentrated under reduced pressure. Column chromatography (silica, 5% MeOH—CH$_2$Cl$_2$) yielded the coumarin analogue (0.007 g, 56%) as a colourless oil; $[\alpha]^{589}_{23}$ +23.0 (c 0.30, CHCl$_3$); IR (CH$_2$Cl$_2$) 3453, 3357, 2965, 2927, 2871, 1713, 1613, 1392, 1325, 1120, 1042, 976, 845 cm$^{-1}$; $^1$H nmr (400 MHz, CDCl$_3$): δ 7.69 (1H, d, J 9.5 Hz, H-3 or H-2), 7.40 (1H, d, J 8.0 Hz, H-7b), 7.25 (2H, m, H-7a, H-6), 6.63 (1H, dt, J 14.0, 10.5 Hz, H-23), 6.43 (1H, d, J 12.0 Hz, H-8), 6.38 (1H, d, J 8.5 Hz, H-3 or H-2), 6.11 (1H, dd, J 11.0, 10.5 Hz, H-22), 5.89 (1H, dd, J 12.0, 11.0 Hz, H-9), 5.50 (1H, t, J 10.0 Hz, H-21), 5.24 (1H, d, J 16.0 Hz, H-24trans), 5.15 (1H, d, J 9.5 Hz, H-24cis), 4.90 (1H, d, J 10.0 Hz, H-13), 4.76 (1H, t, J 6.0 Hz, H-19), 3.27 (1H, dd, J 7.5, 3.5 Hz, H-11), 3.20 (1H, dd, J 5.5, 5.0 Hz, H-17), 3.11-3.04 (2H, m, H-20, H-10), 2.40 (1H, m, H-12), 1.77-1.72 (3H, m, H-18, H-16, 1×H-15), 1.33 (3H, s, H-14'), 1.25 (1H, m, 1×H-15), 1.17 (3H, d, J 7.0 Hz, H-18'), 1.04 (3H, d, J 7.0 Hz, H-10'), 0.94 (3H, d, J 6.5 Hz, H-20'), 0.81 (3H, d, 7.0 Hz, H-12'). 0.74 (3H, d, J 6.0 Hz, H-16'); $^{13}$C nmr (100 MHz, CDCl$_3$): δ 161.1, 157.3, 154.0, 143.1, 141.7, 136.9, 133.6, 132.1, 129.9, 129.1, 128.1, 127.8, 127.4, 124.6, 118.0, 117.2, 116.8, 116.0, 80.1, 78.8, 76.1, 37.2, 36.6, 35.5, 35.2, 34.4, 33.2, 22.7, 18.3, 17.6, 17.1, 14.3, 8.3; m/z 574 [M+Na]$^+$, 534 [M+H—H$_2$O]$^+$, 491 (Found: [M+Na]$^+$, 574.3112. C$_{33}$H$_{45}$NO$_6$ requires [M+Na]$^+$, 574.3139).

Example 2

Preparation of Coumarin Compound (+)-8

A B Coupling to Form C24-C-9 Segment

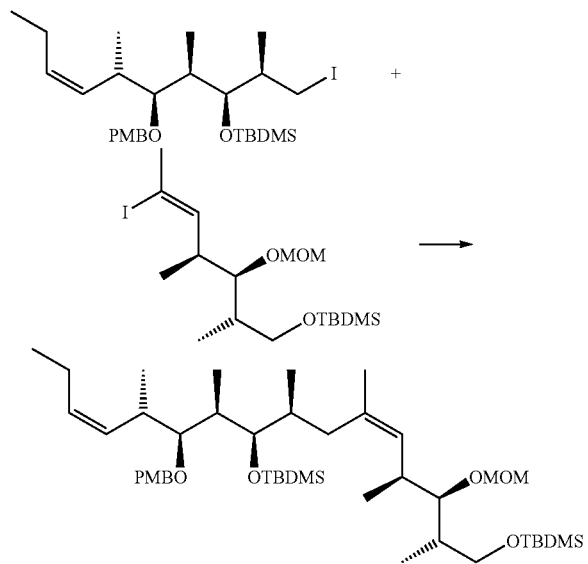

To a solution of the azeotroped alkyl iodide (6.0 g, 10.43 mmol, 1.15 eq) in ether (40 ml) was added zinc chloride (10.4 ml of a 1.0M solution in ether, 10.43 mmol, 1.15 eq). The solution was cooled to −78° C. and degassed three times before adding tert-butyllithium (18.4 ml of a 1.7M solution in pentane, 31.30 mmol, 3.46 eq) dropwise over 10 minutes. After degassing under vacuum and recharging with nitrogen the solution was stirred at room temperature for 1 hour before transferring to an intermate mixture of azeotroped vinyl iodide (4.0 g, 9.07 mmol, 1.00 eq) and tetrakis(triphenylphosphine)palladium (0.5 g, 0.45 mmol, 0.05 eq). The resulting mixture was stirred in the dark for 6 hours at room temperature before quenching with water (60 ml). The mixture was partitioned and the aqueous phase extracted with ether (3×40 ml). The combined organics were dried (MgSO$_4$) and concentrated under reduced pressure. Column chromatography (silica, 5% EtOAc-hexane) yielded the coupled material (3.7 g, 54%) as a colourless oil; $[\alpha]^{589}_{23}$ +23.8 (c 1.10, CH$_2$Cl$_2$); IR (CH$_2$Cl$_2$) 2958, 2930, 2857, 1514, 1462, 1249, 1087, 1035, 834, 772 cm$^{-1}$; $^1$H nmr (400 MHz, CDCl$_3$): δ 7.28 (2H, d, J 8.5 Hz, o-C$_6$H$_4$OMe), 6.86 (2H, d, J 8.5 Hz, m-C$_6$H$_4$OMe), 5.44 (1H, m, H-21), 5.39 (1H, m, H-22), 5.10 (1H, d, J 10.0 Hz, H-13), 4.64 (1H, d AB system, J 6.5 Hz, OCH$_2$OCH$_3$), 4.62 (1H, d AB system, J 6.5 Hz, OCH$_3$OCH$_3$), 4.57 (1H, d AB system, J 10.5 Hz, 1×CH$_2$Ar), 4.44 (1H, d AB system, J 10.5 Hz, 1×CH$_2$Ar), 3.80 (3H, s, ArOCH$_3$), 3.63 (1H, dd, J 9.5, 4.0 Hz, 1×H-9), 3.48 (2H, m, H-17, 1×H-9), 3.40 (3H, s, OCH$_3$), 3.20 (2H, m, H-19, H-11), 2.80 (1H, m, H-20), 2.55 (1H, m, H-12), 2.10 (1H, m, 1×H-15), 2.03 (2H, m, 2×H-23), 1.87-1.79 (3H, m, H-18, H-16, H-10), 1.75 (1H, m, 1×H-15), 1.60 (3H, s, H-14'), 1.04 (3H, d, J 7.0 Hz, H-20'), 1.00 (3H, d, J 7.0 Hz, H-18' or H-10'), 0.97 (3H, t, J 7.5 Hz, H-24), 0.94 (9H, s, 1×SiC(CH$_3$)$_3$), 0.93 (6H, m, H-12', H-18' or H-10'), 0.89 (9H, s, 1×SiC(CH$_3$)$_3$), 0.74 (3H, d, J 6.5 Hz, H-16'), 0.09 (3H, s, 1×SiCH$_3$), 0.08 (3H, s, 1×SiCH$_3$), 0.03 (6H, s, 2×SiCH$_3$); $^{13}$C nmr (100 MHz, CDCl$_3$): δ 159.0, 132.4, 131.4 (2C), 131.3, 130.7, 129.0 (2C), 113.6 (2C), 98.1, 84.7, 84.6, 77.3, 74.7, 65.0, 56.1, 55.3, 39.9, 39.0, 36.3, 35.4, 34.9, 34.1, 26.3, 25.9, 23.2, 20.9, 18.9, 18.6, 18.3, 16.0, 14.4, 14.2, 14.1, 10.8, −3.3, −3.4, −5.4 (2C); m/z 786 [M+Na]$^+$, 611 (Found [M+Na]$^+$, 785.5563, C$_{44}$H$_{82}$O$_6$Si$_2$ requires [M+Na]$^+$ 785.5542).

C24-C-9 Alcohol

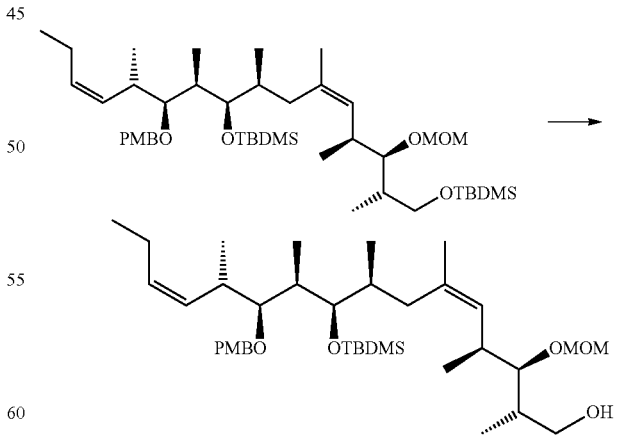

A 1% solution of hydrochloric acid in ethanol (150 ml) was added to the disilyl ether (3.7 g, 4.85 mmol, 1.0 eq). The solution was stirred at room temperature for 35 minutes before adding NaHCO$_3$ (200 ml). The organics were extracted with CHCl$_3$ (3×200 ml), combined, washed with brine (300 ml), dried (MgSO$_4$) and concentrated under reduced pressure. Column chromatography (silica, 15→30% EtOAc-hexane) yielded the alcohol (1.9 g, 60%) as a colourless oil; [α]$^{589}_{23}$ +8.6 (c 1.04, CH$_2$Cl$_2$); IR (CH$_2$Cl$_2$) 3484, 2960, 2932, 1514, 1462, 1249, 1035, 835 cm$^{-1}$; $^1$H nmr (400 MHz, CDCl$_3$): δ 7.26 (2H, d, J 8.5 Hz, o-C$_6$H$_4$OMe), 6.86 (2H, d, J 9.0 Hz, m-C$_6$H$_4$OMe), 5.45 (1H, m, H-21), 5.37 (1H, m, H-22), 5.04 (1H, d, J 10.0 Hz, H-13), 4.65 (2H, s, OCH$_2$OCH$_3$), 4.57 (1H, d AB system, J 11.0 Hz, 1H×OCH$_2$Ar), 4.43 (1H, d AB system, J 11.0 Hz, 1H×OCH$_2$Ar), 3.81 (1H, m, 1×H-9), 3.79 (3H, s, ArOCH$_3$), 3.46 (1H, m, 1×H-9), 3.42 (3H, s, OCH$_3$), 3.24 (1H, dd, J 7.0, 5.0 Hz, H-11), 3.19 (1H, dd, J 6.5, 4.0 Hz, H-19), 2.81 (1H, m, H-20), 2.60 (1H, m, H-12), 2.12-1.98 (3H, m, 2×H-23, 1×H-15), 1.84 (3H, m, H-18, H-16, H-10), 1.74 (1H, m, 1×H-15), 1.66 (3H, d, J 1.0 Hz, H-14'), 1.04 (3H, d, 7.0 Hz, H-20'), 1.01 (3H, d, J 7.0 Hz, H-18'), 1.00 (3H, t, J 7.5 Hz, H-24), 0.94 (9H, s, SiC(CH$_3$)$_3$), 0.93 (3H, m, H-12'), 0.73 (3H, d, J 6.5 Hz, H-16'), 0.09 (3H, s, 1×SiCH$_3$), 0.00 (3H, s, 1×SiCH$_3$); $^{13}$C nmr (100 MHz, CDCl$_3$): δ 159.0, 133.3, 131.4, 131.4, 131.2, 130.2, 129.0 (2C), 113.7 (2C), 99.1, 87.4, 84.5, 77.2, 65.0, 56.3, 55.3, 40.0, 37.3, 36.4, 35.4, 34.9, 34.7, 26.3, 23.2, 20.9, 18.9, 18.6, 15.3, 15.1, 14.4, 14.2, 10.8, −3.3; m/z 671 [M+Na]$^+$ (Found [M+Na]$^+$, 671.4664, C$_{38}$H$_{68}$O$_6$Si requires [M+Na]$^+$ 671.4677).

C-24-C-9 Phosphonium Salt

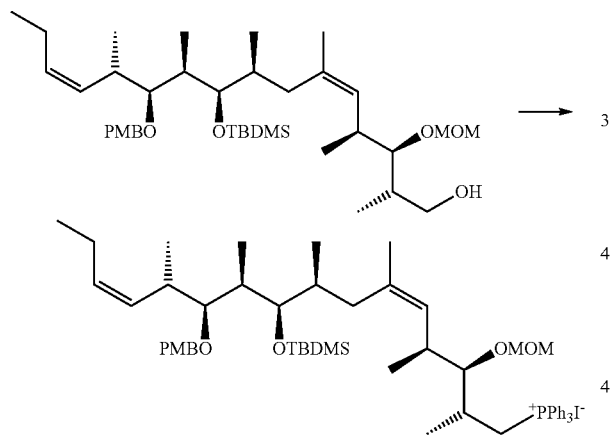

A solution of the alcohol (1.9 g, 2.93 mmol, 1.0 eq), triphenylphosphine (1.2 g, 4.39 mmol, 1.5 eq) and imidazole (0.3 g, 4.39 mmol, 1.5 eq) in ether-benzene (1:2, 45 ml) was cooled to 0° C. and iodine (1.1 g, 4.39 mmol, 1.5 eq) added. The solution was stirred at 0° C. for 30 minutes before warming to room temperature and stirring for 45 minutes. The solution was diluted with EtOAc (50 ml) and poured into NaHCO$_3$:Na$_2$S$_2$O$_3$ (4:1, 50 ml). The organics were partitioned and the aqueous phase extracted with EtOAc (3×50 ml). The combined organics were dried (MgSO$_4$) and concentrated under reduced pressure. Column chromatography (silica, 15% EtOAc-hexane) yielded the iodide contaminated with triphenylphosphine, which was taken on without characterisation.

To the crude iodide (2.93 mmol) was added triphenylphosphine (7.7 g, 29.30 mmol, 10.0 eq) followed by diisopropylethylamine (14.6 ml). The mixture was heated to 100° C. for 17 hours before cooling and placing onto a silica column. Column chromatography (silica, 20% EtOAc-hexane, then 20→50% CH$_3$CN—CH$_2$Cl$_2$) yielded the phosphonium salt (1.8 g, 62% over 2 steps) as a white solid; [α]$^{589}_{23}$ +16.1 (c 1.16, CH$_2$Cl$_2$); IR (CH$_2$Cl$_2$) 2960, 2932, 1514, 1462, 1438, 1248, 1110, 1027, 918, 835 cm$^{-1}$; $^1$H nmr (400 MHz, CDCl$_3$): δ 7.81-7.69 (15H, m, P(C$_6$H$_5$)$_3$), 7.24 (2H, d, J 8.5 Hz, o-C$_6$H$_4$OCH$_3$), 6.83 (2H, d, J 8.5 Hz, m-C$_6$H$_4$OCH$_3$), 5.39 (1H, m, H-21), 5.27 (1H, m, H-22), 5.02 (1H, d, J 10.0 Hz, H-13), 4.68 (1H, d AB system, J 6.0 Hz, OCH$_2$O), 4.63 (1H, d AB system, J 6.0 Hz, OCH$_2$O), 4.54 (1H, d AB system, J 10.5 Hz, OCH$_2$C$_6$H$_4$O), 4.39 (1H, d AB system, J 10.5 Hz, OCH$_2$C$_6$H$_4$O), 3.75 (3H, s, ArCH$_3$), 3.72 (1H, m, 1×H-9), 3.39 (1H, t, J 4.0 Hz, H-17), 3.32 (3H, s, OCH$_3$), 3.28 (1H, dd, J 6.0, 5.5 Hz, H-11), 3.15 (1H, dd, J 7.0, 3.5 Hz, H-19), 3.09 (1H, dd, J 10.5, 4.0 Hz, 1×H-9), 2.75 (1H, m, H-20), 2.48 (1H, m, H-12), 2.13 (1H, m, H-10), 2.06 (1H, m, 1×H-23), 2.00-1.91 (2H, m, 1×H-23, 1×H-15), 1.74-1.69 (2H, m, H-18, H-16), 1.57 (1H, m, 1×H-15), 1.49 (3H, s, H-14'), 1.01 3H, d, J 7.0 Hz, H-20'), 0.91 (3H, d, J 7.0 Hz, H-18'), 0.90 (3H, t, J 7.5 Hz, H-24), 0.87 (9H, s, SiC(CH$_3$)$_3$), 0.82 (3H, d, J 6.5 Hz, H-12'), 0.73 (3H, d, 7.0 Hz, H-10'), 0.64 (3H, d, J 6.5 Hz, H-16'), 0.04 (6H, s, 2×SiCH$_3$), 0.00 (6H, s, 2×SiCH$_3$); $^{13}$C nmr (100 MHz, CDCl$_3$): δ 159.0, 135.8, 133.9, 133.5 (d, J 9.0 Hz), 131.3, 131.2, 131.0, 130.7, (d, J 12.0 Hz), 129.0 (2C), 118.4 (d, J 80.0 Hz), 113.7 (2C), 99.3, 88.1 (d, J 12.0 Hz), 84.5, 77.0, 74.8, 56.2, 55.3, 39.7, 35.9, 35.4, 34.8, 34.2, 31.6, 26.2, 23.0, 20.9, 18.9, 18.7, 18.5, 18.0, 17.4, 15.5, 14.6, 14.4, 12.6, 10.8, −3.3, −3.4; m/z 894 [M]$^+$ (Found [M]$^+$, 893.5623, C$_{56}$H$_{82}$O$_5$SiP requires [M]$^+$ 893.5664).

Coupling with 7-Carboxaldehyde-Coumarin

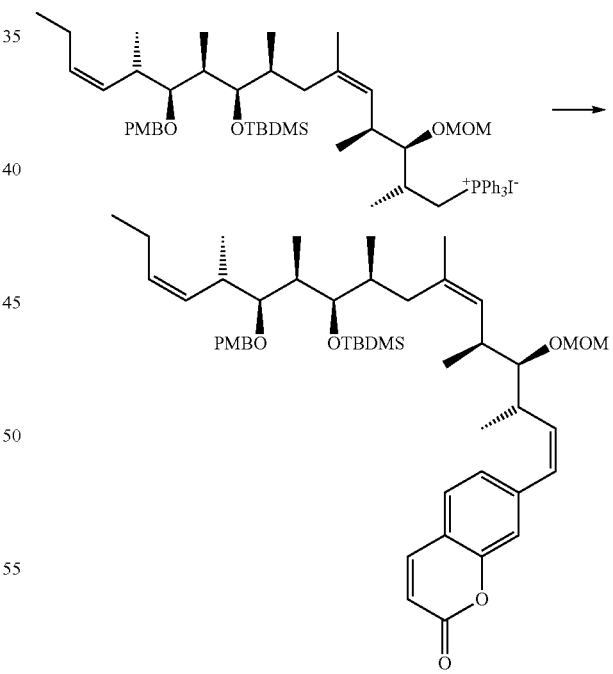

Using a similar Wittig coupling procedure with 7-carboxycoumarin on a 0.59 mmol scale yielded the coupled material (0.015 g, 32%) as a colourless oil; [α]$^{589}_{22}$ +109.5 (c 0.75, CHCl$_3$); IR (CHCl$_3$) 2960, 2930, 2876, 1737, 1614, 1514, 1248, 1098, 1037, 836 cm$^{-1}$; $^1$H nmr (400 MHz, CDCl$_3$): δ 7.58 (1H, d, J 9.5 Hz, H-3 or H-2), 7.32-7.27 (4H, m, o-C$_6$H$_4$OCH$_3$, H-7b, H-6), 7.18 (1H, dd, J 8.0, 1.5 Hz, H-7a), 6.87 (2H, d, J 8.5 Hz, m-C$_6$H$_4$OCH$_3$), 6.37 (1H, d, J 12.5 Hz, H-8), 6.34 (1H, d, J 9.5 Hz, H-3 or H-2), 5.87 (1H, dd, J 12.0, 10.5 Hz, H-9), 5.47 (1H, dd, J 11.0, 9.5 Hz, H-21), 5.36 (1H, dt, J 11.0, 7.0 Hz, H-22), 4.92 (1H, d, J 10.0 Hz, H-13), 4.69 (2H, s, OCH$_2$O), 4.57 (1H, d AB system, J 10.5 Hz, 1×OCH$_2$Ar), 4.43 (1H, d AB system, J 10.5 Hz, 1×OCH$_2$Ar), 3.80 (3H, s, ArOCH$_3$), 3.42 (3H, s, OCH$_3$), 3.40 (1H, m, H-17), 3.16 (2H, m, H-19, H-11), 3.12 (1H, m, H-10), 2.79-2.75 (1H, m, H-20), 2.50-2.44 (1H, m, H-12), 2.04 (2H, m, 2×H-23), 1.95 (1H, m, 1×H-15), 1.76-1.68 (2H, m, H-18, H-16), 1.40 (1H, m, 1×H-15), 1.38 (3H, s, H-14'), 1.10 (3H, d, J 7.0 Hz, H-10'), 1.05 (3H, d, J 7.0 Hz, H-20'), 0.96 (3H, t, J 7.5 Hz, H-24), 0.94 (3H, d, J 7.0 Hz, H-12'), 0.92 (3H, d, J 7.0 Hz, H-18'), 0.91 (9H, s, SiC(CH$_3$)$_3$), 0.67 (3H, d, J 6.5 Hz, H-16'), 0.08 (3H, s, 1×SiCH$_3$), 0.05 (3H, s, 1×SiCH$_3$); $^{13}$C nmr (100 MHz, CDCl$_3$): δ 161.0, 159.0, 154.1, 143.1, 141.7, 138.0, 133.4, 131.5, 131.4, 131.1, 129.8, 129.0 (2C), 127.4, 127.1, 125.5, 117.1, 115.9 (2C), 113.7 (2C), 98.6, 87.9, 84.8, 74.8, 56.2, 55.3, 39.7, 36.0, 35.8, 35.6, 35.2, 34.8, 29.7, 26.2 (3C), 22.8, 20.9, 18.9, 18.6, 18.3, 17.0, 14.7, 14.3, 10.6, −3.3, −3.4.

or H-2), 7.39 (1H, d, J 8.0 Hz, H-7b), 7.32 (1H, br s H-6), 7.20 (1H, dd, J 8.0, 1.5 Hz, H-7a), 6.37 (2H, m, H-8, H-3 or H-2), 5.87 (1H, dd, J 12.0, 10.5 Hz, H-9), 5.55 (1H, dt, J 11.0, 7.5 Hz, H-22), 5.19 (1H, dd, J 10.5, 10.0 Hz, H-21), 4.95 (1H, d, J 10.0 Hz, H-13), 4.70 1H, d AB system, J 7.0 Hz, 1×OCH$_2$O), 4.68 (1H, d AB system, J 7.0 Hz, 1×OCH$_2$O), 3.56 (1H, dd, J 6.0, 3.0 Hz, H-17), 3.41 (3H, s, OCH$_3$), 3.23 (1H, m, H-19), 3.20 (1H, m, H-11), 3.13 (1H, m, H-10), 2.61 (1H, m, H-20), 2.52 (1H, dt, J 10.0, 7.0 Hz, H-12), 2.16-2.04 (3H, 2×H-23, 1×H-15), 1.79-1.71 (2H, m, H-18, H-16), 1.48 (1H, m, 1×H-15), 1.44 (3H, s, H-14'), 1.09 (3H, d, J 7.0 Hz, H-10'), 0.98 (3H, t, J 7.5 Hz, H-24), 0.94 (3H, d, H 7.0 Hz, H-12'), 0.91-0.89 (6H, m, H-20', H-18'), 0.89 (9H, s, SiC(CH$_3$)$_3$), 0.70 (3H, d, J 7.0 Hz, H-16'), 0.07 (3H, s, 1×SiCH$_3$), 0.05 (3H, s, 1×SiCH$_3$); $^{13}$C nmr (100 MHz, CDCl$_3$): δ 161.0, 154.1, 143.1, 141.7, 138.1, 134.1, 133.8, 131.7, 129.6, 127.4, 127.1, 125.2, 117.2, 116.1, 115.9, 98.6, 87.9, 78.9, 76.0, 56.2, 37.8, 36.3, 35.9, 35.7, 35.6, 34.6, 26.2 (3C), 23.0, 21.0, 18.4, 18.3, 17.2, 16.9, 14.4, 13.4, 9.4, −3.3, −3.7.

Carbamate Formation

Deprotection of the PMB Ether

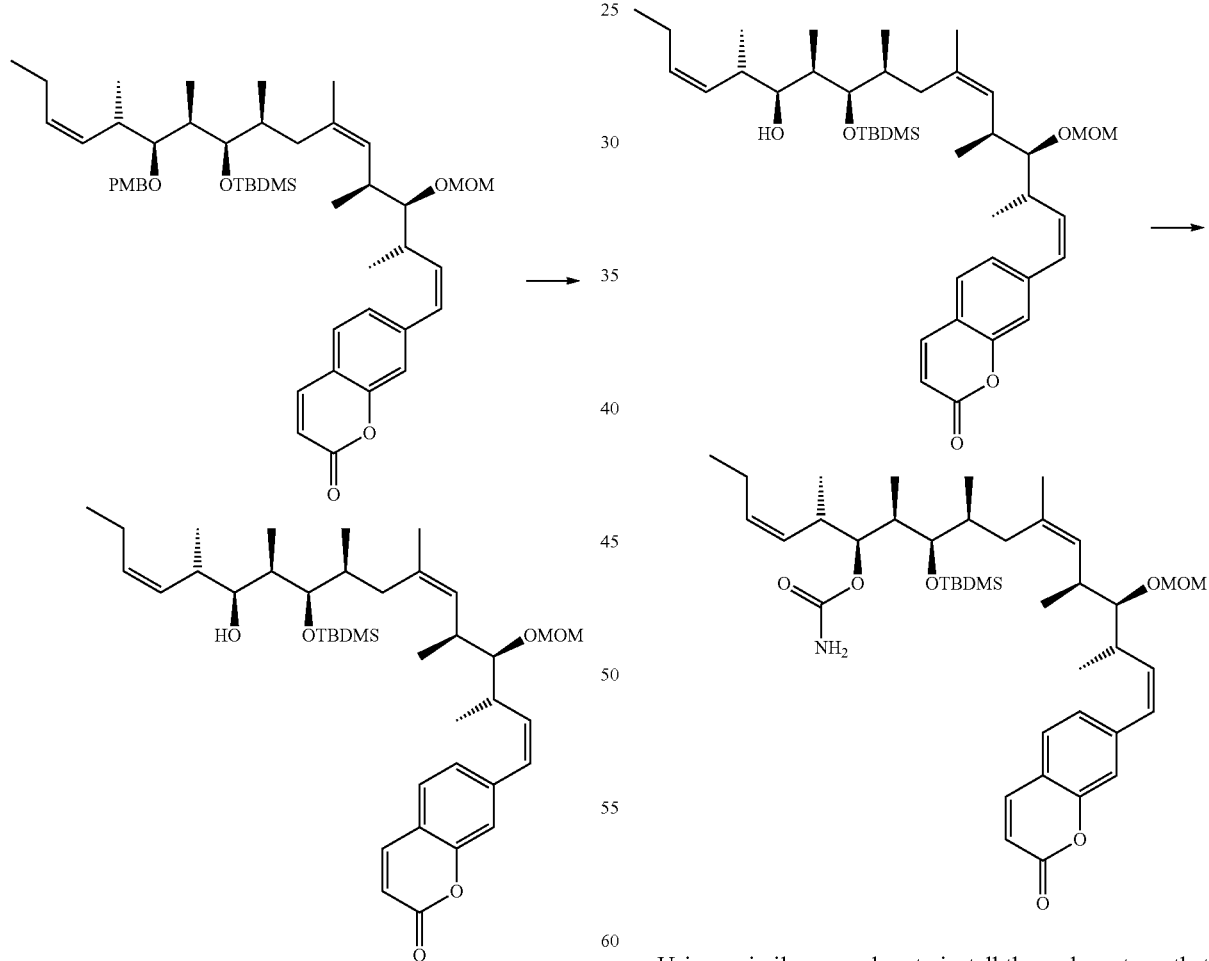

Using a similar deprotection procedure on a 0.018 mmol scale yielded the alcohol (0.010 g, 84%) as a pale yellow oil; [α]$^{589}_{22}$ +86.1 (c 0.70, CHCl$_3$); IR (CHCl$_3$) 3398, 2961, 2927, 2876, 1736, 1615, 1462, 1255, 1099, 1038, 837, 773 cm$^{-1}$; $^1$H nmr (400 MHz, CDCl$_3$): δ 7.66 (1H, d, J 9.5 Hz, H-3

Using a similar procedure to install the carbamate as that described above on a 0.013 mmol scale yielded the carbamate (0.005 g, 54%) as a colourless oil; [α]$^{589}_{22}$ +35.2 (c 0.50, CHCl$_3$); IR (CHCl$_3$) 3662, 2961, 2929, 1728, 1614, 1462, 1375, 1327, 1255, 1097, 1036, 837, 773 cm$^{-1}$; $^1$H nmr (400 MHz, CDCl$_3$): δ 7.69 (1H, d, J 9.5 Hz, H-3 or H-2), 7.40 (1H, d, J 8.0 Hz, H-7b), 7.24 (2H, m, H-7a, H-6), 6.38 (1H, d, J 9.5

Hz, H-3 or H-2), 6.36 (1H, d, J 12.0 Hz, H-8), 5.89 (1H, dd, J 12.0, 10.5 Hz, H-9), 5.41 (1H, m, H-22), 5.33 (1H, dd, J 11.0, 10.5 Hz, H-21), 4.84 (1H, d, J 10.0, Hz, H-13), 4.71 (3H, br s, OCH$_2$O, NH$_2$), 4.67 (1H, dd, J 6.5, 6.0 Hz, H-19), 3.43 (3H, s, OCH$_3$), 3.33 (1H, dd, J 6.5, 5.0 Hz, H-17), 3.15 (2H, m, H-11, H-10), 2.78 (1H, m, H-20), 2.43 (1H, m, H-12), 2.08-2.00 (2H, m, 2×H-23), 1.95 (1H, dd, J 12.5, 12.0 Hz, 1×H-15), 1.79 (1H, m, H-18), 1.74 (1H, m, H-16), 1.30 (3H, s, H-14'), 1.26 (1H, m, 1×H-15), 1.15 (3H, d, J 6.5 Hz, H-10'), 0.99 (3H, t, J 7.5 Hz, H-24), 0.95 (3H, d, J 6.5 Hz, H-20' or H-12'), 0.93 (3H, d, J 6.5 Hz, H-20' or H-12'), 0.90 (9H, s, SiC(CH$_3$)$_3$), 0.82 (3H, d, J 7.0 Hz, H-18'), 0.66 (3H, d, J 6.5 Hz, H-16'), 0.10 (3H, s, 1×SiCH$_3$), 0.07 (3H, s 1×SiCH$_3$); $^{13}$C nmr (100 MHz, CDCl$_3$): δ 157.1, 143.2, 141.8, 137.7, 136.3, 133.6, 132.1, 130.5, 129.3, 127.4, 127.1, 124.7, 117.1, 116.5, 115.9, 98.8, 88.3, 78.6, 56.2, 37.8, 36.4, 35.6, 34.7, 33.8, 26.2 (3C), 22.5, 20.8, 18.5, 18.4, 17.8, 17.4, 14.5, 14.0, 9.9, −3.4 (2C); m/z 734 [M+Na]$^+$, 580 (Found [M+Na]$^+$, 734.4447, C$_{41}$H$_{65}$NO$_7$Si requires [M+Na]$^+$ 734.4423).

Deprotection to the 7-Coumarin Compound

Using the Deprotection procedure on a 0.007 mmol scale yielded the deprotected compound (0.002 g, 51%) as a colourless oil; [α]$^{589}_{22}$ +20.1 (c 0.21, CHCl$_3$); IR (CHCl$_3$) 3444, 3362, 2962, 2926, 2855, 1711, 1612, 1459, 1378, 1043, 976, 846, 733 cm$^{-1}$; $^1$H nmr (400 MHz, CDCl$_3$): δ 7.69 (1H, d, J 9.5 Hz, H-3 or H-2), 7.40 (1H, d, J 8.0 Hz, H-7b), 7.28 (1H, br s, H-6), 7.25 (1H, m, H-7a), 6.43 (1H, d, J 9.5, H-3 or H-2), 6.38 (1H, d, J 11.5 Hz, H-9), 5.45 (1H, m, H-22), 5.41 (1H, m, H-21), 4.92 (1H, d, J 9.0 Hz, H-13), 4.73 (1H, t, J 6.0 Hz, H-19), 3.28 (1H, dd, J 7.5, 4.0 Hz, H-11), 3.19 (1H, t, J 5.5 Hz, H-17), 3.10 (1H, m, H-10), 2.85 (1H, m, H-12), 2.13-2.01 (2H, m, 2×H-23), 1.83-1.78 (2H, m, H-18, 1×H-15), 1.71 (1H, m, H-16), 1.36 (3H, s, H-14'), 1.30 (1H, m, 1×H-15), 1.17 (3H, d, J 7.0 Hz, H-10'), 1.01 (3H, t, J 7.5 Hz, H-24), 0.99 (3H, d, J 7.0 Hz, H-20'), 0.96 (3H, d, J 6.5 Hz, H-12'), 0.79 (3H, d, J 7.0 Hz, H-18'), 0.76 (3H, d, J 6.0 Hz, H-16'); $^{13}$C nmr (100 MHz, CDCl$_3$): δ 161.3, 157.4, 154.0, 143.2, 141.5, 136.8, 133.7, 132.3, 130.4, 129.1, 127.8, 127.4, 124.6, 117.2, 116.8, 116.0, 80.0, 79.0, 76.2, 37.3, 36.6, 35.5, 35.3, 33.9, 33.2, 22.8, 20.8, 18.2, 17.9, 17.0, 14.5, 14.4, 8.3; m/z 576 [M+Na]$^+$, 536 [M+H—H$_2$O]$^+$, 493, 475 (Found [M+Na]$^+$, 576.3310, C$_{33}$H$_{47}$NO$_6$ requires [M+Na]$^+$ 576.3296).

Example 3

Preparation of Lactam 11

Wittig Coupling to Form the N-Methylcoumarin Lactam

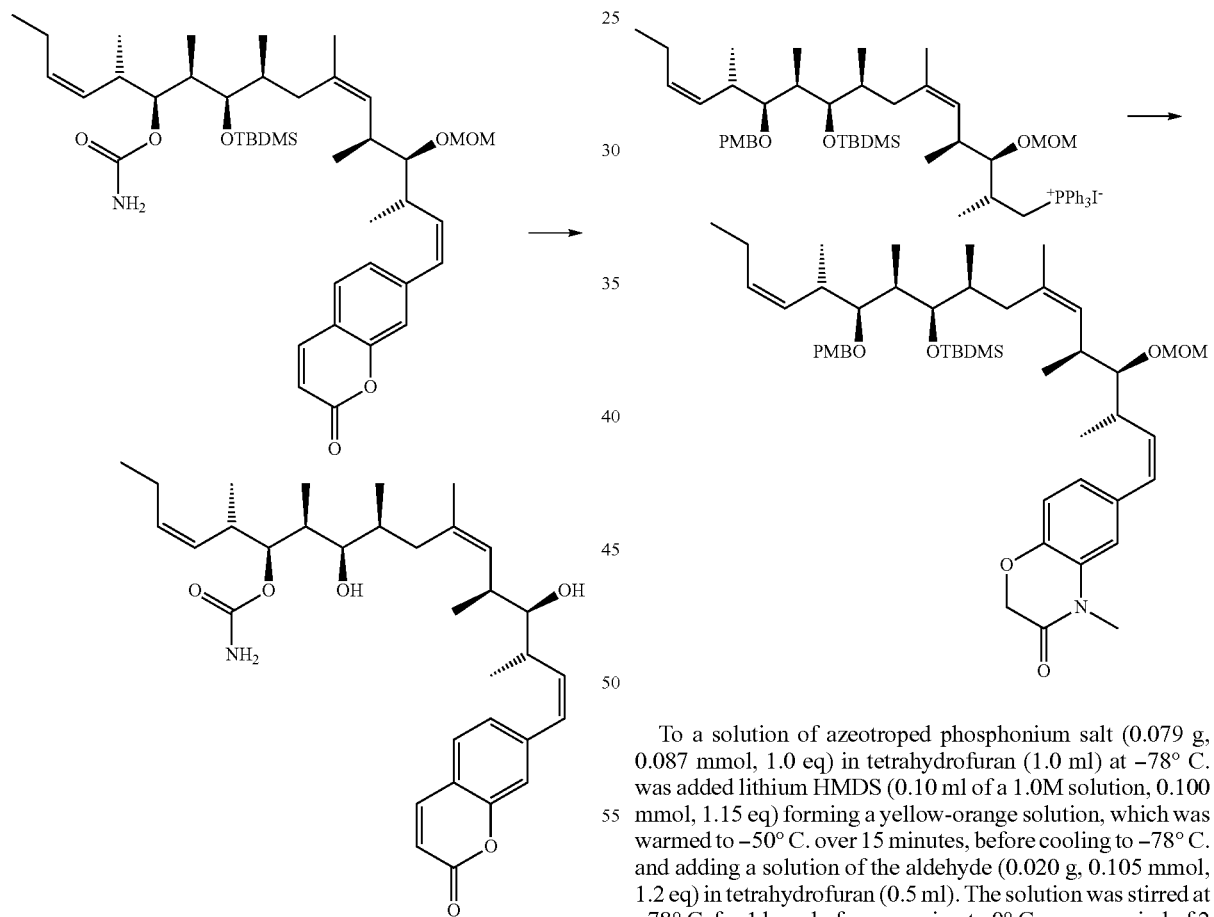

To a solution of azeotroped phosphonium salt (0.079 g, 0.087 mmol, 1.0 eq) in tetrahydrofuran (1.0 ml) at −78° C. was added lithium HMDS (0.10 ml of a 1.0M solution, 0.100 mmol, 1.15 eq) forming a yellow-orange solution, which was warmed to −50° C. over 15 minutes, before cooling to −78° C. and adding a solution of the aldehyde (0.020 g, 0.105 mmol, 1.2 eq) in tetrahydrofuran (0.5 ml). The solution was stirred at −78° C. for 1 hour before warming to 0° C. over a period of 2 hours. NH$_4$Cl (10 ml) was added and the organics extracted with EtOAc (3×15 ml). The combined organics were dried (MgSO$_4$) and concentrated under reduced pressure. Column chromatography (silica, 20% EtOAc-hexane, then 20% CH$_3$CN—CH$_2$Cl$_2$) yielded the coupled compound (0.025 g, 36%) as a colourless oil; [α]$^{589}_{23}$ +77.6 (c 0.60, CH$_2$Cl$_2$); IR (CH$_2$Cl$_2$) 2960, 2930, 1692, 1609, 1514, 1462, 1371, 1249, 1037, 834 cm$^{-1}$; $^1$H nmr (400 MHz, CDCl$_3$): δ 7.27 (2H, d, J 8.5 Hz, o-OC$_6$H$_4$OCH$_3$), 7.06 (1H, d, J 1.5 Hz, H-6), 6.97 (1H, dd, J 8.5, 1.5 Hz, H-7a), 6.88 (1H, d, J 8.5 Hz, H-7b), 6.86 (2H, d, J 8.5 Hz, m-OC$_6$H$_4$OCH$_3$), 6.32 (1H, d, J 12.0 Hz, H-8), 5.62 (1H, dd, J 11.5, 10.5 Hz, H-9), 5.45 (1H, m, H-21), 5.37 (1H, m, H-22), 5.02 (1H, d, J 10.0 Hz, H-13), 4.67 (2H, s, OCH$_2$O), 4.59 (2H, s, 2×H-2), 4.56 (1H, d AB system, J 10.5 Hz, 1×OCH$_2$Ar), 4.45 (1H, d AB system, 1×OCH$_2$Ar), 3.80 (3H, s, ArCH$_3$), 3.41 (1H, m, H-17), 3.40 (3H, s, OCH$_3$), 3.33 (3H, s, NCH$_3$), 3.19 (2H, m, H-19, H-11), 3.11-3.05 (1H, m, H-10), 2.82-2.77 (1H, m, H-20), 2.57-2.51 (1H, m, H-12), 2.11-1.98 (3H, m, 2×H-23, 1×H-15), 1.80-1.73 (2H, m, H-18, H-16), 1.52 (1H, m, 1×H-15), 1.47 (3H, s, H-14'), 1.05 (3H, d, J 6.0 Hz, H-20'), 1.03 (3H, d, J 6.5 Hz, H-10'), 0.97 (3H, t, J 7.5 Hz, H-24), 0.95 (3H, d, J 7.5 Hz, H-18'), 0.94 (3H, m, H-12'), 0.93 (9H, s, SiC(CH$_3$)$_3$), 0.70 (3H, J 6.5 Hz, H-16'), 0.08 (3H, s, 1×SiCH$_3$), 0.07 (3H, s, 1×SiCH$_3$); $^{13}$C nmr (100 MHz, CDCl$_3$): δ 164.5, 159.0, 143.7, 135.0, 133.1, 132.5, 131.4, 131.1, 130.1, 129.0 (2C), 127.5, 124.2, 116.4, 115.0, 113.7 (2C), 98.4, 87.5, 84.6, 74.8, 67.6, 56.2, 55.3, 39.8, 36.0, 35.5, 35.3, 35.2, 34.8, 27.9, 26.3 (3C), 23.0, 20.9, 18.9, 18.6, 18.3, 16.2, 14.7, 14.4, 10.6, −3.3 (2C); m/z 829 [M+Na]$^+$ (Found [M+Na]$^+$, 828.5185, C$_{48}$H$_{75}$NO$_7$Si requires [M+Na]$^+$ 828.5205); and recovered phosphonium salt; data agrees with that stated above.

Deprotection of the PMB Ether

To a solution of the PMB protected compound (0.024 g, 0.030 mmol, 1.0 eq) in dichloromethane (1.0 ml) was added water (0.3 ml) and the mixture cooled to 0° C. before adding 2,3-dichloro-5,6-dicyanobenzoquinone (0.010 g, 0.045 mmol, 1.5 eq). The mixture was stirred at 0° C. for 30 minutes and at room temperature for 1 hour before adding NaHCO$_3$ (10 ml). The organics were extracted with CH$_2$Cl$_2$ (30 ml), washed with water (20 ml) and brine (20 ml), before drying (MgSO$_4$) and concentrating under reduced pressure. Column chromatography (silica, 20% EtOAc-hexane) yielded the deprotected material (0.012 g, 58%) as a colourless oil; [α]$^{589}_{23}$ +79.3 (c 0.15, CH$_2$Cl$_2$); IR (CH$_2$Cl$_2$) 3509, 2961, 2927, 2881, 1692, 1474, 1373, 1251, 1090, 1039, 835 cm$^{-1}$; $^1$H nmr (400 MHz, CDCl$_3$): δ 7.08 (1H, d, J 1.0 Hz, H-6), 6.98 (1H, dd, J 8.5, 1.5 Hz, H-7a), 6.91 (1H, d, J 8.0 Hz, H-7b), 6.33 (1H, d, J 11.5 Hz, H-8), 5.65 (1H, dd, J 11.5, 11.0 Hz, H-9), 5.56 (dt, J 11.0, 7.5 Hz, H-22), 5.18 (1H, dd, J 10.5, 10.0 Hz, H-21), 5.04 (1H, d, J 9.0 Hz, H-13), 4.69 (1H, d AB system, J 6.5 Hz, 1×OCH$_2$O), 4.67 (1H, d AB system, J 6.5 Hz, 1×OCH$_2$O), 4.60 (2H, s, OCH$_2$CO), 3.58 (1H, dd, J 10.5, 3.0 Hz, H-17), 3.40 (3H, s, OCH$_3$), 3.36 (3H, s, NCH$_3$), 3.25-3.21 (2H, m, H-19, H-11), 3.09 (1H, m, H-10), 2.65-2.58 (2H, m, H-20, H-12), 2.18 (1H, t, J 12.0 Hz, 1×H-15), 2.07 (2H, m, 2×H-23), 1.86 (1H, m, H-16), 1.77 (1H, td, J 7.0, 2.5 Hz, H-18), 1.63 (1H, br d, J 11.5 Hz, 1×H-15), 1.52 (3H, s, H-14'), 1.04 (3H, d, J 7.0 Hz, H-10'), 0.99 (3H, t, J 8.5 Hz, H-24), 0.95 (3H, d, J 7.0 Hz, H-12'), 0.93-0.90 (6H, m, H-20', H-18'), 0.91 (9H, s, SiC(CH$_3$)$_3$), 0.72 (3H, d, J 7.0 Hz, H-16'), 0.08 (3H, s, 1×SiCH$_3$), 0.08 (3H, s, 1×SiCH$_3$); $^{13}$C nmr (100 MHz, CDCl$_3$): δ 164.6, 143.7, 135.2, 134.3, 133.5, 132.6, 131.7, 130.0, 129.1, 127.5, 124.1, 116.4, 115.1, 98.4, 87.5, 79.0, 75.9, 67.6, 562, 37.8, 36.6, 35.8, 35.5, 35.1, 34.6, 28.0, 26.2 (3C), 23.2, 21.0, 18.5, 18.3, 17.1, 16.1, 14.4, 13.2, 9.5, −3.2, −3.6; m/z 708 [M+Na]$^+$ (Found [M+Na]$^+$, 708.4639, C$_{40}$H$_{67}$NO$_6$Si requires [M+Na]$^+$ 708.4630);

Introduction of Carbamate

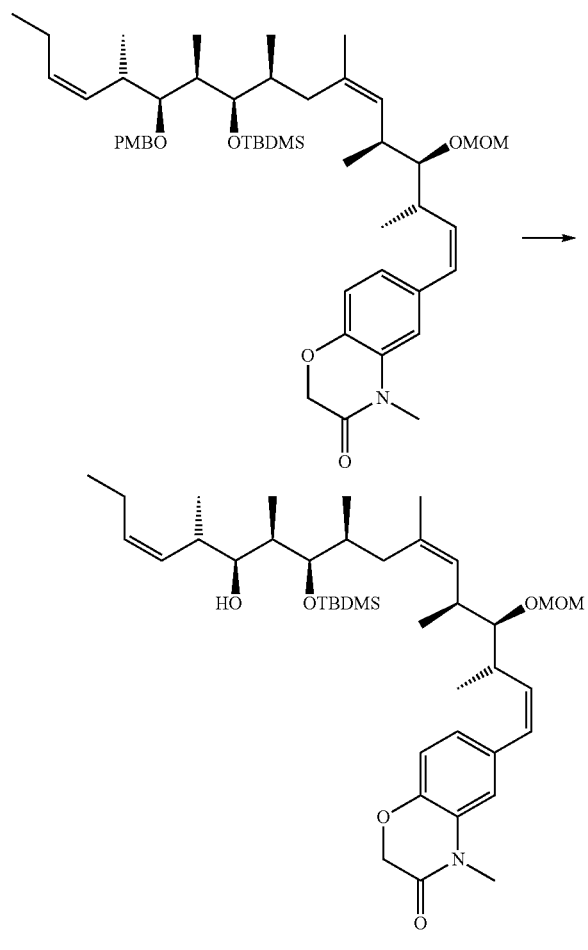

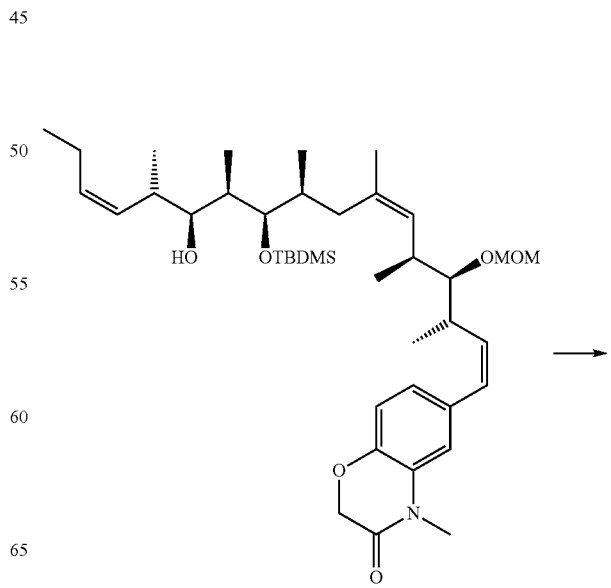

-continued

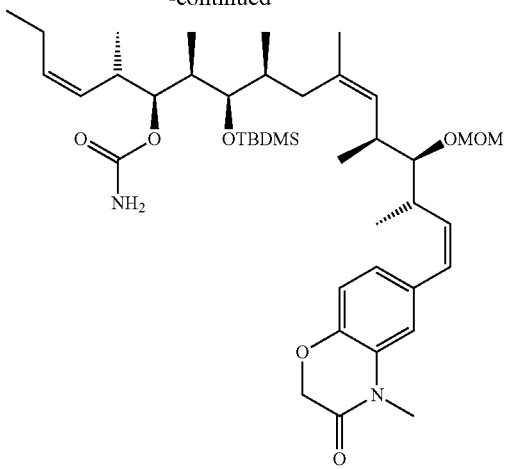

To a solution of the alcohol (0.011 g, 0.016 mmol, 1.0 eq) in dichloromethane (0.5 ml) was added trichloroacetyl isocyanate (0.030 g, 0.019 ml, 0.160 mmol, 10.0 eq). The solution was stirred at room temperature for 50 minutes, before concentrating under reduced pressure. The residue was cooled to 0° C. and dissolved in methanol (1.0 ml). Freshly ground potassium carbonate (0.10 g) was added. The solution was stirred at 0° C. for 1 hour before warming to room temperature over 2 hours. The solution was partitioned between EtOAc (15 ml) and water (15 ml). The aqueous phase was extracted with EtOAc (3×15 ml). The combined organics were dried (MgSO$_4$) and concentrated under reduced pressure. Column chromatography (silica, 20% EtOAc-hexane) yielded the carbamate (0.010 g, 86%) as a colourless oil; $[\alpha]^{589}_{22}$ +53.7 (c 0.67, CHCl$_3$); IR (CHCl$_3$) 3484, 3357, 2962, 2932, 2881, 1728, 1683, 1605, 1474, 1373, 1094, 1037, 835 cm$^{-1}$; $^1$H nmr (400 MHz, CDCl$_3$): δ 7.02 (1H, d, J 1.5 Hz, H-6), 6.98 (1H, dd, J 8.5, 1.5 Hz, H-7a), 6.91 (1H, d, J 8.5 Hz, H-7b), 6.31 (1H, d, J 12.0 Hz, H-8), 5.64 (1H, dd, J 11.5, 10.5 Hz, H-9), 5.39 (1H, dt, J 11.0, 7.0 Hz, H-22), 5.26 (1H, dd, 11.0, 10.0 Hz, H-21), 4.96 (1H, d, J 10.0 Hz, H-13), 4.69 (3H, s, OCH$_2$O), 4.65 (1H, dd, J 6.5, 5.5 Hz, H-19), 4.62 (3H, OCH$_2$CO), 4.60 (2H, br s, NH$_2$), 3.41 (3H, s, OCH$_3$), 3.36 (3H, s, NCH$_3$), 3.35 (1H, m, H-17), 3.18 (1H, dd, J 6.5, 6.0 Hz, H-11), 3.10 (1H, m, H-10), 2.78 (1H, dt, J 9.5, 6.5 Hz, H-20), 2.51 (1H, dt, J 10.0, 6.5 Hz, H-12), 2.10-1.97 (3H, m, 2×H-23, 1×H-15), 1.86-1.80 (2H, m, H-18, H-16), 1.45 (3H, s, H-14'), 1.44 (1H, m, 1×H-15), 1.08 (3H, d, J 7.0 Hz, H-10'), 0.98 (3H, t, J 7.5 Hz, H-24), 0.94 (3H, d, J 6.5 Hz, H-20' or H-12'), 0.93 (3H, d, J 7.0 Hz, H-20' or H-12'), 0.92 (9H, s, SiC(CH$_3$)$_3$), 0.88 (3H, d, J 7.0 Hz, H-18'), 0.68 (3H, d, J 6.5 Hz, H-16'), 0.09 (3H, s, 1×SiCH$_3$), 0.08 (3H, s, 1×SiCH$_3$); $^{13}$C nmr (100 MHz, CDCl$_3$): δ 164.9, 156.9, 143.7, 134.8, 133.4, 132.5, 132.1, 130.5, 129.7, 129.0, 127.5, 123.9, 116.3, 115.2, 98.6, 87.9, 78.7, 67.7, 56.2, 37.8, 36.2, 35.5, 35.4, 34.8, 28.0, 26.2 (3C), 22.8, 20.8, 18.5, 18.4, 17.8, 16.6, 14.4, 13.4, 10.2, −3.3, −3.5; m/z 751 [M+Na]$^+$ (Found, [M+Na]$^+$, 751.4678, C$_{41}$H$_{68}$N$_2$O$_7$Si requires [M+Na]$^+$ 751.4688).

Deprotection to Generate the Final Compound

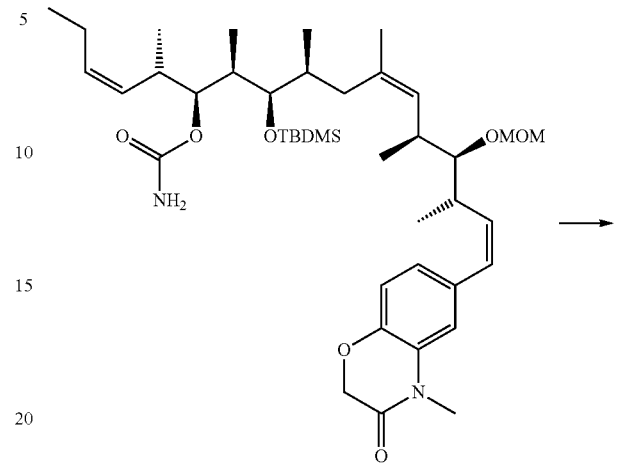

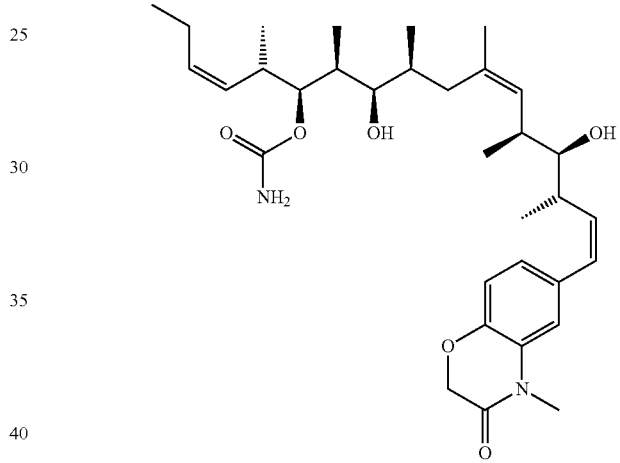

To a solution of the protected compound (0.009 g, 0.012 mmol, 1.0 eq) in methanol (1.5 ml) was added hydrochloric acid (3.0 M, 2×0.5 ml) in two aliquots over 30 minutes. After stirring for a further 30 minutes MeOH (0.5 ml) was added followed by hydrochloric acid (4.5M, 0.5 ml) and the solution stirred for 1 hour before adding further hydrochloric acid (4.5M, 0.5 ml) and stirring for 2 hours. The mixture was poured into a mixture of water (15 ml) and EtOAc (15 ml). The solution was neutralized with NaHCO$_3$ (solid), and partitioned. The aqueous phase was extracted with EtOAc (3×15 ml) and the combined organics were washed with brine (30 ml) and dried (MgSO$_4$) before concentrating under reduced pressure. Column chromatography (silica, 55% EtOAc-hexane) yielded the deprotected compound (0.003 g, 43%) as a colourless oil; $[\alpha]^{589}_{22}$ +76.0 (c 0.20, CHCl$_3$); IR (CHCl$_3$) 3453, 3352, 2962, 2932, 2871, 1712, 1676, 1606, 1477, 1459, 1376, 1322, 1231, 1044, 969 cm$^{-1}$; $^1$H nmr (400 MHz, CDCl$_3$): δ 7.02 (1H, d, J 1.5 Hz, H-6), 7.00 (1H, dd, J 8.0, 1.5 Hz, H-7a), 6.92 (1H, d, J 8.0 Hz, H-7b), 6.42 (1H, d, J 12.0 Hz, H-8), 5.60 (1H, dd, J 11.5, 10.5 Hz, H-9), 5.42 (1H, dt, J 11.0, 7.5 Hz, H-22), 5.26 (1H, dd, J 11.0, 10.0 Hz, H-21), 5.10 (1H, d, J 9.5 Hz, H-13), 4.71 (1H, dd, J 6.5, 4.5 Hz, H-19), 4.61 (2H, br s, NH$_2$), 4.61 (2H, s, OCH$_2$CO), 3.37 (3H, s, NCH$_3$), 3.30 (1H, dd, J 6.0, 5.5 Hz, H-17), 3.19 (1H, t, J 5.5 Hz, H-11), 3.07 (1H, dt, J 10.5, 6.5 Hz, H-10), 2.82 (1H, m, H-20), 2.59 (1H, m, H-12), 2.13-2.00 (2H, m, 2×H-23), 1.87-1.80 (3H, m, H-18, H-16, 1×H-15), 1.63 (1H, m, 1×H-15), 1.52 (3H, d, J 1.0 Hz, H-14'), 1.09 (3H, d, J 7.0 Hz, H-10'), 0.98 (3H, t, J 7.5 Hz, H-24), 0.96 (3H, d, J 6.5 Hz, H-12'), 0.95 (3H, d, J 7.0 Hz, H-20'), 0.90 (3H, d, J 7.0 Hz, H-18'), 0.79 (3H, d, J 6.0 Hz, H-16'); $^{13}$C nmr (100 MHz, CDCl$_3$): δ 164.6, 157.0, 143.9, 134.1, 133.8, 132.3 (2C), 130.4, 129.2, 129.1, 128.9, 124.1, 116.4, 115.3, 79.8, 78.9, 76.0, 67.6, 37.2, 35.7, 35.6, 34.2, 32.8, 29.7, 28.1, 23.1, 20.8, 18.1, 17.8, 16.3, 14.5, 13.8, 8.8; m/z 593 [M+Na]$^+$, 571 [M+H]$^+$, 553 [M+H—H$_2$O]$^+$, 510, 492 (Found, [M+Na]$^+$ 593.3565, $C_{33}H_{50}N_2O_6$ requires [M+Na]$^+$ 593.3561).

Example 4

Preparation of Lactams 10 and 12

Coupling with N-MOM-2-dihydro-3-oxy-coumarinamide-6-carboxaldehyde

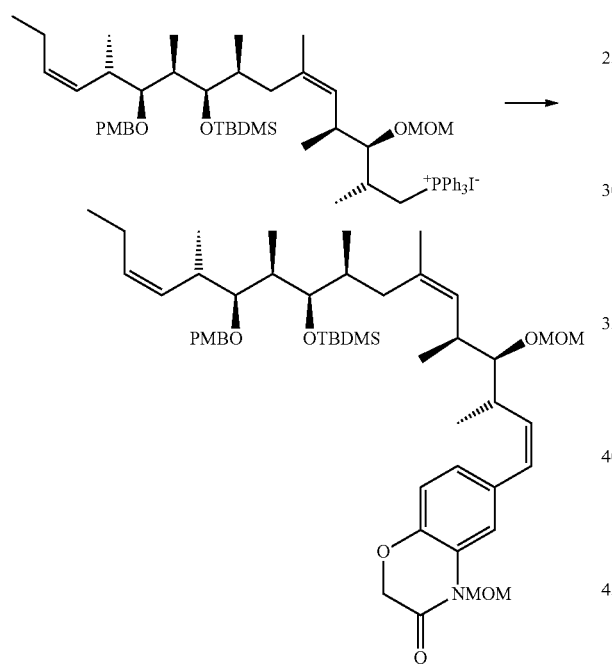

Using a similar Wittig coupling procedure with N-MOM-2-dihydro-3-oxy-coumarinamide-6-carboxaldehyde on a 0.095 mmol scale yielded the coupled material (0.060 g, 76%) as a colourless oil; $[α]^{589}_{20}$ +71.4 (c 1.15, CHCl$_3$); IR 2959, 2930, 1699, 1611, 1513, 1448, 1371, 1248, 1079, 1037, 834, 772 cm$^{-1}$; $^1$H nmr (400 MHz, CDCl$_3$): δ 7.28 (3H, m, H-6, o-C$_6$H$_4$OMe), 7.00 (1H, dd, J 8.5, 1.5 Hz, H-7a), 6.88 (2H, d, J 8.0 Hz, m-C$_6$H$_4$OMe), 6.87 (1H, d, J 8.5 Hz, H-7b), 6.31 (1H, d, J 12.0 Hz, H-8), 5.64 (1H, dd, J 11.5, 10.5 Hz, H-9), 5.47 (1H, m, H-21), 5.37 (1H, m, H-22), 5.31 (1H, d AB system, J 10.5 Hz, 1H of H-2), 5.25 (1H, d AB system, 1H of H-2), 4.98 (1H, d, J 10.0 Hz, H-13), 4.67 (2H, s, OCH$_2$O or NCH$_2$O or ArCH$_2$O), 4.60 (2H, s, OCH$_2$O or NCH$_2$O or ArCH$_2$O), 4.56 (1H, d AB system, J 10.5 Hz, 1H×OCH$_2$O or NCH$_2$O or ArCH$_2$O), 4.45 (1H, d AB system, J 10.5 Hz, 1H×OCH$_2$O or NCH$_2$O or ArCH$_2$O), 3.80 (3H, s, ArOCH$_3$), 3.40 (3H, s, 1×OCH$_3$), 3.39 (1H, m, H-17), 3.38 (3H, s, 1×OCH$_3$), 3.20-3.17 (2H, m, H-19, H-11), 3.08 (1H, m, H-10), 2.78 (1H, m, H-20), 2.52 (1H, m, H-12), 2.11-1.96 (3H, m, 2×H-23, 1×H-15), 1.80-1.71 (2H, m, H-18, H-16), 1.49 (1H, m, 1×H-15), 1.44 (3H, s, H-14'), 1.06 (3H, d, J 7.0 Hz, H-20' or H-10'), 1.05 (3H, d, J 6.5 Hz, H-20' or H-10'), 0.97 (3H, t, J 7.5 Hz, H-24), 0.95-0.93 (6H, m, H-18', H-12'), 0.93 (9H, s, SiC(CH$_3$)$_3$), 0.69 (3H, d, J 6.5 Hz, H-16'), 0.09 (3H, s, 1×SiCH$_3$), 0.07 (3H, s, 1×SiCH$_3$); $^{13}$C nmr (100 MHz, CDCl$_3$): δ 165.5, 143.6, 134.9, 133.1, 132.8, 131.4 (2C), 131.1, 130.0, 129.9 (2C), 127.5, 124.9, 116.5, 116.1, 113.7 (2C), 98.4, 87.7, 84.6, 74.8, 72.7, 67.5, 56.3, 56.1, 55.3, 39.8, 35.9, 35.4 (2C), 35.3, 34.8, 29.7, 26.3 (3C), 23.0, 20.9, 18.9, 18.6, 18.2, 16.4, 14.6, 14.4, 10.6, -3.3 (2C); m/z 859 [M+Na]$^+$ (Found, [M+Na]$^+$ 858.5354, $C_{49}H_{77}NO_8Si$ requires [M+Na]$^+$ 858.5311).

Deprotection of the PMB Ether

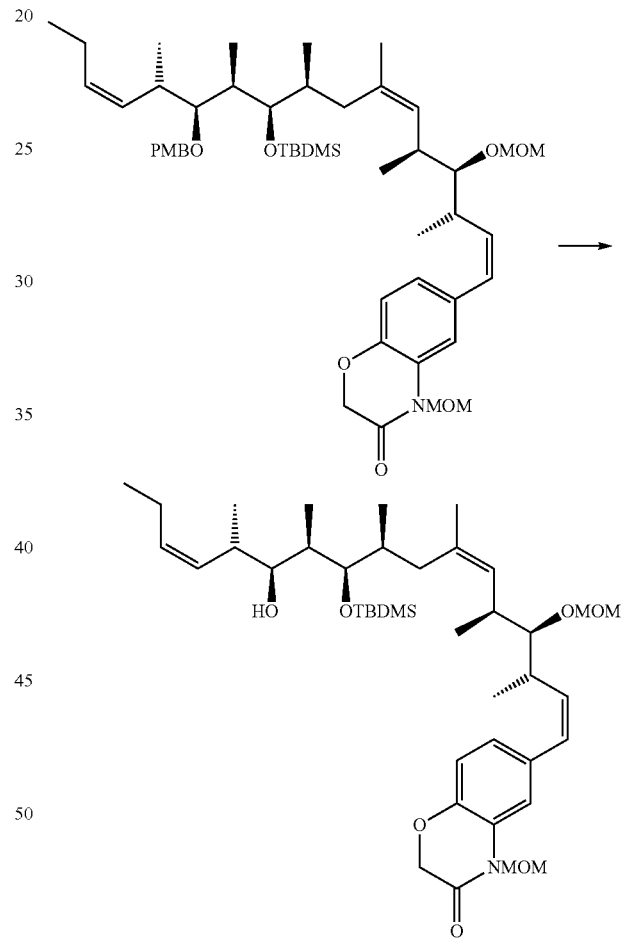

Using a similar deprotection procedure on a 0.067 mmol scale yielded the alcohol as a colourless oil contaminated with benzaldehyde, which was used without further purification; $^1$H nmr (400 MHz, CDCl$_3$): δ 7.28 (1H, d, J 2.0 Hz, H-6), 7.00 (1H, m, H-7a), 6.96 (1H, d, J 8.5 Hz, H-7b), 6.31 (1H, d, J 12.0 Hz, H-8), 5.66 (1H, dd, J 12.0, 10.5 Hz, H-9), 5.55 (1H, dt, J 10.5, 7.5 Hz, H-22), 5.34 (1H, d AB system, J 10.5 Hz, 1H×H-2), 5.27 (1H, d AB system, J 10.5 Hz, 1H×H-2), 5.18 (1H, dd, J 11.0, 10.0 Hz, H-21), 4.98 (1H, d, J 10.0 Hz, H-13), 4.69 (1H, d AB system, J 7.0 Hz, 1H×OCH$_2$O), 4.67 (1H, d AB system, J 7.0 Hz, 1H×OCH$_2$O), 4.61 (2H, s, NCH$_2$O), 3.58 (1H, dd, J 6.5, 2.5 Hz, H-17), 3.40 (6H, s, 2×OCH$_3$), 3.24 (1H, m, H-19), 3.21 (1H, m, H-11), 3.08 (1H, m, H-10), 2.62-2.53 (2H, m, H-20, H-12), 2.16 (1H, t, J 12.0 Hz, 1×H-15), 2.07 (2H, m, 2×H-23), 1.84 (1H, m, H-16), 1.76 (1H, td, J 6.5, 3.0 Hz, H-18), 1.62 (1H, m, 1×H-15), 1.48 (3H, s, H-14'), 1.07 (3H, d, J 7.0 Hz, H-10'), 0.99 (3H, t, J 7.5 Hz, H-24), 0.95 (3H, d, J 6.5 Hz, H-12'), 0.93-0.90 (6H, m, H-20', H-18'), 0.91 (9H, s, SiC(CH$_3$)$_3$), 0.71 (3H, d, J 7.0 Hz, H-16'), 0.08 (6H, s, 2×SiCH$_3$); $^{13}$C nmr (100 MHz, CDCl$_3$): δ 165.6, 143.6, 135.0, 134.2, 133.4, 132.9, 131.7, 129.9, 127.9, 127.5, 124.8, 116.5, 116.3, 98.4, 87.8, 79.0, 75.9, 72.8, 67.5, 56.4, 56.1, 37.8, 36.5, 35.8, 35.4, 34.6, 26.2 (3C), 23.1, 21.0, 18.5, 18.2, 17.2, 16.4, 14.4, 13.2, 9.5, −3.2, −3.6; m/z 738 [M+Na]$^+$ (Found, [M+Na]$^+$ 738.4740, C$_{41}$H$_{69}$NO$_7$Si requires [M+Na]$^+$ 738.4736).

Introduction of the Carbamate

Hz, 1×H-2), 4.94 (1H, d, J 10.0 Hz, H-13), 4.68 (2H, s, OCH$_2$O), 4.66 (1H, m, H-19), 4.64 (2H, s, NH$_2$), 4.62 (2H, s, NCH$_2$O), 3.40 (6H, 2s, 2×OCH$_3$), 3.36 (1H, dd, J 5.0, 4.5 Hz, H-17), 3.17 (1H, dd, J 5.5, 5.0 Hz, H-11), 3.12-3.06 (1H, m, H-10), 2.78 (1H, dt, J 9.5, 6.5 Hz, H-20), 2.51 (1H, dt, J 10.0, 6.5 Hz, H-12), 2.09-1.97 (3H, m, 2×H-23, 1×H-15), 1.86-1.77 (2H, m, H-18, H-16), 1.46 (1H, m, 1×H-15), 1.45 (3H, s, H-14'), 1.08 (3H, d, J 7.0 Hz, H-10'), 0.97 (3H, t, J 7.5 Hz, H-24), 0.94 (3H, d, J 7.0 Hz, H-20' or H-12'), 0.93 (3H, d, J 6.5 Hz, H-20' or H-12'), 0.91 (9H, s, SiC(CH$_3$)$_3$), 0.88 (3H, d, J 7.0 Hz, H-18'), 0.69 (3H, d, J 6.5 Hz, H-16'), 0.09 (3H, s, 1×SiCH$_3$), 0.07 (3H, s, 1×SiCH$_3$); $^{13}$C nmr (100 MHz, CDCl$_3$): δ 165.7, 157.1, 143.7, 134.8, 133.3, 132.8, 132.1, 130.4, 129.8, 127.9, 127.5, 124.8, 116.4, 116.3, 98.4, 87.9, 78.9, 72.8, 67.6, 56.3, 56.1, 37.8, 36.0, 35.6, 35.4, 34.9, 33.9, 26.2 (3C), 22.8, 20.8, 18.5, 18.2, 17.8, 16.6, 14.4, 13.6, 10.2, −3.3, −3.6; m/z 781 [M+Na]$^+$ (Found, [M+Na]$^+$ 781.4777, C$_{42}$H$_{70}$N$_2$O$_8$Si requires [M+Na]$^+$ 781.4794).

N-MOM Compound (12) by Selective Deprotection of Hydroxyls

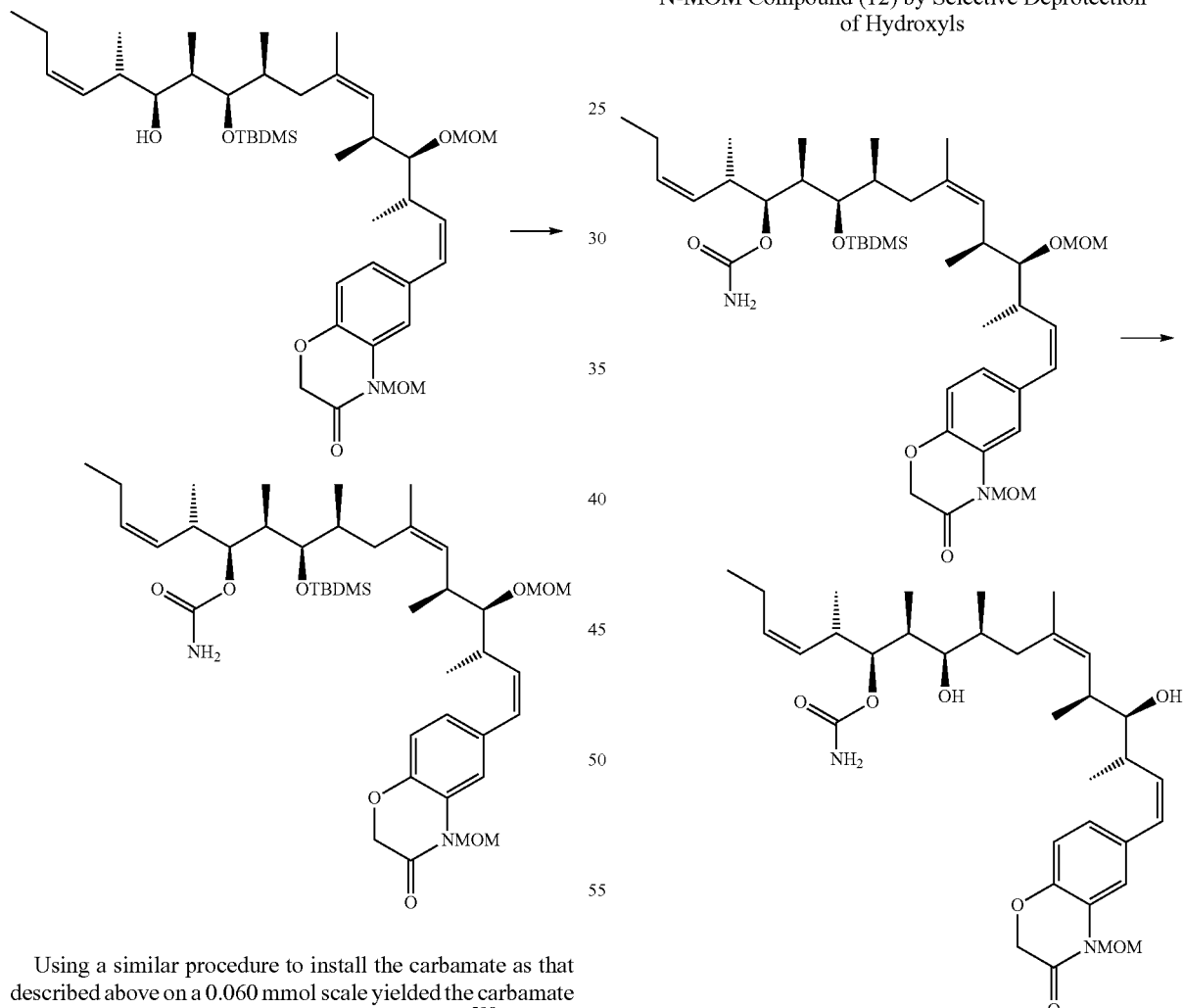

Using a similar procedure to install the carbamate as that described above on a 0.060 mmol scale yielded the carbamate (0.027 g, 53% over 2 steps) as a colourless oil; [α]$^{589}_{22}$ +63.2 (c 1.00, CHCl$_3$); IR (CH$_2$Cl$_2$) 3489, 3362, 2962, 2932, 2881, 1724, 1700, 1606, 1449, 1372, 1081, 1037, 835, 773 cm$^{-1}$; $^1$H nmr (400 MHz, CDCl$_3$): δ 7.26 (1H, m, H-6), 7.01 (1H, dd, J 8.5, 1.5 Hz, H-7a), 6.91 (1H, d, J 8.5 Hz, H-7b), 6.29 (1H, d, J 12.0 Hz, H-8), 5.65 (1H, dd, J 11.5, 10.5 Hz, H-9), 5.39 (1H, dt, J 11.0, 7.0 Hz, H-22), 5.33 (1H, d AB system, J 10.5 Hz, 1×H-2), 5.29 (1H, m, H-21), 5.26 (1H, d AB system, J 10.5

Using the Deprotection procedure on a 0.033 mmol scale yielded the N-MOM protected compound (0.006 g, 30%) as a colourless oil; [α]$^{589}_{21}$ +51.2 (c 0.60, CHCl$_3$); IR (CH$_2$Cl$_2$) 3452, 3357, 2963, 2932, 2873, 1689, 1607, 1510, 1449, 1373, 1320, 1285, 1080, 1044, 971, 737 cm$^{-1}$; $^1$H nmr (400 MHz, CDCl$_3$): δ 7.26 (1H, m, H-6), 7.03 (1H, dd, J 8.5, 2.0 Hz, H-7a), 6.93 (1H, d, J 8.5 Hz, H-7b), 6.41 (1H, d, J 12.0 Hz, H-8), 5.61 (1H, dd, J 11.5, 10.5 Hz, H-9), 5.42 (1H, dt, J 11.0, 7.0 Hz, H-22), 5.31 (2H, s, 2×H-2), 5.27 (1H, dd, J 11.0, 10.0, H-21), 5.07 (1H, d, J 10.5 Hz, H-13), 4.70 (1H, dd, J 7.0, 4.5 Hz, H-19), 4.62 (2H, NCH$_2$O), 4.59 (2H, NH$_2$), 3.42 (3H, s, OCH$_3$), 3.29 (1H, dd, J 6.5, 5.5 Hz, H-11), 3.19 (1H, br t, J 5.0 Hz, H-17), 3.04 (1H, dt, J 10.0, 6.5 Hz, H-10), 2.82 (1H, dt, J 10.0, 7.0 Hz, H-20), 2.56 (1H, dt, J 10.0, 6.5, Hz, H-12), 2.09-2.03 (2H, m, 2×H-23), 1.90-1.81 (3H, H-18, H-16, 1×H-15), 1.62 (1H, m, 1×H-15), 1.52 3H, d, J 1.0 Hz, H-14'), 1.10 (3H, d, J 6.5 Hz, H-10'), 0.98 (3H, t, J 7.5 Hz, H-24), 0.96 (3H, d, J 6.5 Hz, H-20' or H-12'), 0.94 (3H, d, J 6.5 Hz, H-20' or H-12'), 0.92 (3H, d, J 7.0 Hz, H-18'), 0.79 (3H, d, J 6.0 Hz, H-16'); $^{13}$C nmr (100 MHz, CDCl$_3$): δ 165.5, 157.0, 143.8, 134.1, 133.6, 133.2, 132.6, 130.4, 129.4, 128.7, 127.9, 124.9, 116.5, 116.4, 79.8, 79.0, 76.2, 72.8, 67.6, 56.4, 37.2, 35.6 (3C), 34.2, 32.9, 23.1, 20.8, 17.9, 17.8, 16.2, 14.5, 13.8, 8.8; m/z 623 [M+Na]$^+$, 569, 506 (Found, [M+Na]$^+$ 623.3678, C$_{34}$H$_{52}$N$_2$O$_7$ requires [M+Na]$^+$ 623.3667) and intermediate deprotection products (0.017 g).

N-MOM Deprotection to the N—H Lactam (10)

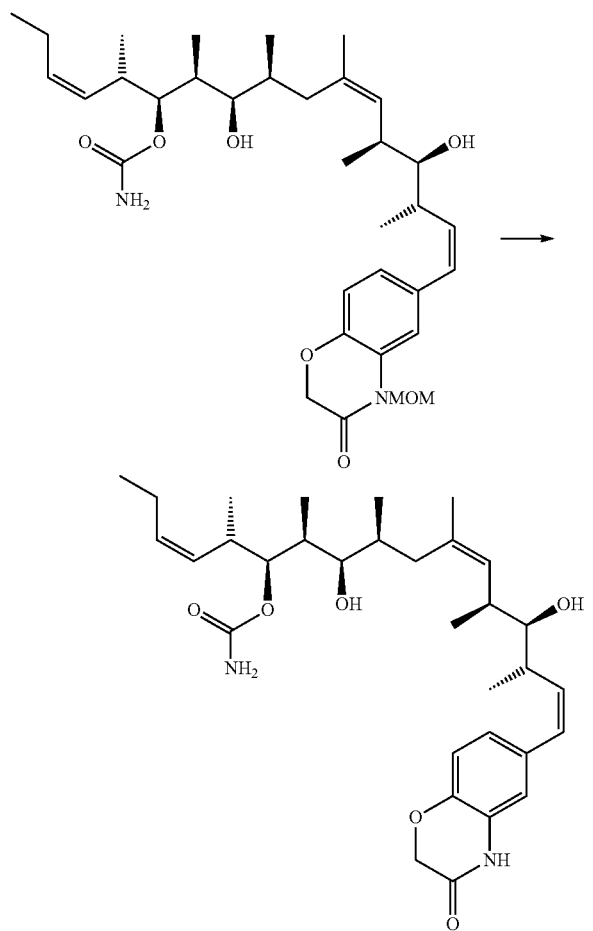

The intermediate deprotected products (0.017 g) were dissolved in methanol (3 ml) and hydrochloric acid (6M, 3×1 ml) added in aliquots over 1 hour. The solution was stirred at room temperature for 36 hours before diluting with EtOAc (20 ml) and neutralizing by the slow addition of NaHCO3 (20 ml). The mixture was partitioned and the aqueous phase extracted with EtOAc (3×20 ml). The combined organics were dried (MgSO4) and concentrated under reduced pressure. Column chromatography (silica, 50% EtOAc-hexane) yielded the deprotected compound (0.004 g, %) as a colourless oil; [α]$^{589}_{20}$ −12.1 (c 0.35, CHCl$_3$); IR (CH$_2$Cl$_2$) 3364, 2964, 2930, 2871, 1694, 1598, 1489, 1457, 1390, 1328, 1044, 991, 968, 734 cm$^{-1}$; $^1$H nmr (400 MHz, CDCl$_3$): δ 8.31 (1H, s, NH), 6.93 (1H, dd, J 8.5, 1.5 Hz, H-7a), 6.90 (1H, d, J 8.0 Hz, H-7b), 6.80 (1H, d, J 1.5 Hz, H-6), 6.30 (1H, d, J 12.0 Hz, H-8), 5.67 (1H, t, J 12.0 Hz, H-9), 5.52 (1H, dt, J 12.0, 7.0 Hz, H-22), 5.38 (1H, dd, J 12.0, 10.0, Hz, H-21), 4.87 (1H, d, J 10.0 Hz, H-13), 4.81 (1H, t, J 5.0 Hz, H-19), 4.62 (1H, d AB system, J 15.5 Hz, 1×H-2), 4.56 (1H, d AB system, J 15.5 Hz, 1×H-2), 3.25 (1H, m, H-17), 3.22 (1H, dd, J 8.0, 3.5 Hz, H-11), 3.00 (1H, m, H-10), 2.90 (1H, dt, J 9.5, 6.5 Hz, H-20), 2.41 (1H, 1H, dt, J 9.0, 7.0 Hz, H-12), 2.15-2.06 (2H, m, 2×H-23), 1.87-1.72 (3H, m, H-18, H-16, 1×H-15), 1.37 (3H, d, J 1.0 Hz, H-14'), 1.32 (1H, m, 1×H-15), 1.16 (3H, d, J 7.0 Hz, H-10'), 1.02 (3H, t, J 7.5 Hz, H-24), 1.01 (3H, d, J 7.0 Hz, H-20'), 0.97 (3H, d, J 6.5 Hz, H-12'), 0.87 (3H, 3H, d, J 7.0 Hz, H-18'), 0.77 (3H, d, J 6.0 Hz, H-16'); $^{13}$C nmr (100 MHz, CDCl$_3$): δ 165.7, 157.7, 142.3, 133.3, 133.1, 132.9, 132.6, 130.4, 129.3, 128.1, 125.5, 123.9, 116.7, 116.4, 80.2, 79.6, 76.0, 67.4, 37.7, 36.9, 35.6, 35.3, 33.8, 33.3, 22.8, 20.9, 18.7, 18.2, 17.5, 14.5, 14.2, 8.6; m/z 579 [M+Na]$^+$, 539 [M+H—H$_2$O]$^+$, 496, 478 (Found, [M+Na]$^+$ 579.3402, C$_{32}$H$_{48}$N$_2$O$_6$ requires [M+Na]$^+$ 579.3405).

Example 6

Preparation of Coumarin Compound 9

Coupling with the 6-Carboxaldehyde Coumarin

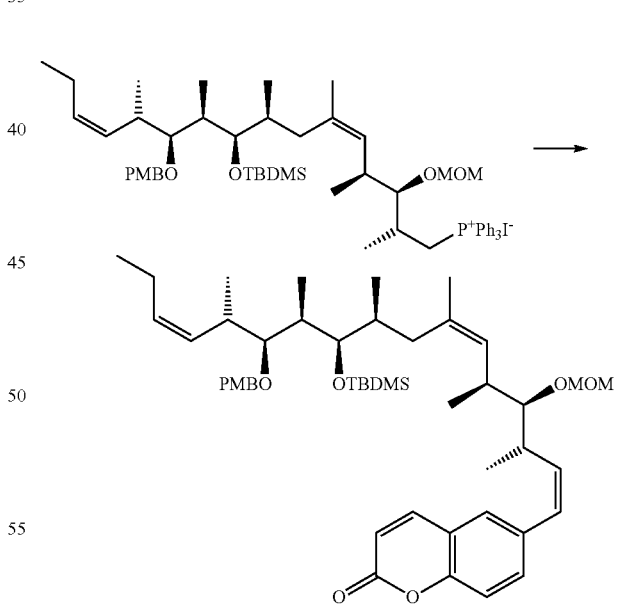

Using a similar Wittig coupling procedure to that above on a 0.074 mmol scale yielded the coupled material (0.012 g, 21%) as a colourless oil; [α]$^{589}_{22}$ +68.8 (c 1.00, CHCl$_3$); IR (CHCl$_3$) 2959, 2948, 2856, 1734, 1570, 1514, 1461, 1249, 1096, 1035, 824, 772 cm$^{-1}$; $^1$H nmr (400 MHz, CDCl$_3$): δ 7.59 (1H, d, J 9.5 Hz, H-3 or H-2), 7.46 (1H, dd, J 8.5, 2.0 Hz, H-7), 7.42 (1H, br s, H-7b), 7.30 (2H, d, J 8.5 Hz, o-C$_6$H$_4$OCH$_3$), 7.21 (1H, d, J 8.5 Hz, H-6), 6.88 (2H, d, J 8.5

Hz, m-C$_6$H$_4$OCH$_3$), 6.34 (1H, d, J 12.0 Hz, H-8), 6.23 (1H, d, J 9.5 Hz, H-3 or H-2), 5.74 (1H, dd, J 12.0, 10.5 Hz, H-9), 5.53 (1H, dd, J 10.5, 10.0 Hz, H-21), 5.42 (1H, dt, J 11.0, 7.0 Hz, H-22), 4.89 (1H, d, J 10.0 Hz, H-13), 4.71 (1H, d AB system, J 7.0 Hz, 1×OCH$_2$O), 4.69 (1H, d AB system, J 7.0 Hz, 1×OCH$_2$O), 4.60 (1H, d AB system, J 10.5 Hz, 1×OCH$_2$Ar), 4.44 (1H, d AB system, J 10.5 Hz, 1×OCH$_2$Ar), 3.81 (3H, s, ArOCH$_3$), 3.42 (3H, s, OCH$_3$), 3.37 (1H, dd, J 5.5, 3.5 Hz, H-17), 3.20 (1H, dd, J 7.5, 3.5 Hz, H-19), 3.17 (1H, dd, J 7.5, 4.0 Hz, H-11), 3.08 (1H, m, H-10), 2.80 (1H, m, H-20), 2.46 (1H, dt, J 10.0, 7.0 Hz, H-12), 2.12-1.99 (2H, m, 2×H-23), 1.90 (1H, t, J 12.5 Hz, 1×H-15), 1.72 (1H, m, H-18), 1.63 (1H, m, H-16), 1.34 (3H, s, H-14'), 1.26 (1H, m, 1×H-15), 1.10 (3H, d, J 7.0 Hz, H-20' or H-10'), 1.09 (3H, d, J 7.0 Hz, H-20' or H-10'), 0.99 (3H, t, J 7.5 Hz, H-24), 0.93 (3H, d, J 6.5 Hz, H-18'), 0.91 (9H, s, SiC(CH$_3$)$_3$), 0.88 (3H, d, J 7.0 Hz, H-12'), 0.67 (3H, d, J 6.5 Hz, H-16'), 0.09 (3H, s, 1×SiCH$_3$), 0.07 (3H, s, 1×SiCH$_3$); $^{13}$C nmr (100 MHz, CDCl$_3$): δ 159.1, 143.7, 135.7, 134.1, 133.2, 132.0, 131.5, 131.4, 130.9, 129.7, 129.0 (2C), 127.6, 126.7, 116.5 (2C), 113.7 (2C), 98.5, 87.8, 84.8, 75.1, 56.1, 55.3, 39.8, 36.0, 35.6, 35.4, 35.0, 34.7, 26.3 (3C), 22.8, 20.9, 19.0, 18.6, 18.2, 17.1, 15.2, 14.5, 10.3, −3.2, −3.4; m/z 811 [M+Na]$^+$ (Found [M+Na]$^+$, 811.4967, C$_{48}$H$_{72}$O$_7$Si requires [M+Na]$^+$ 811.4940).

Deprotection of the PMB Group

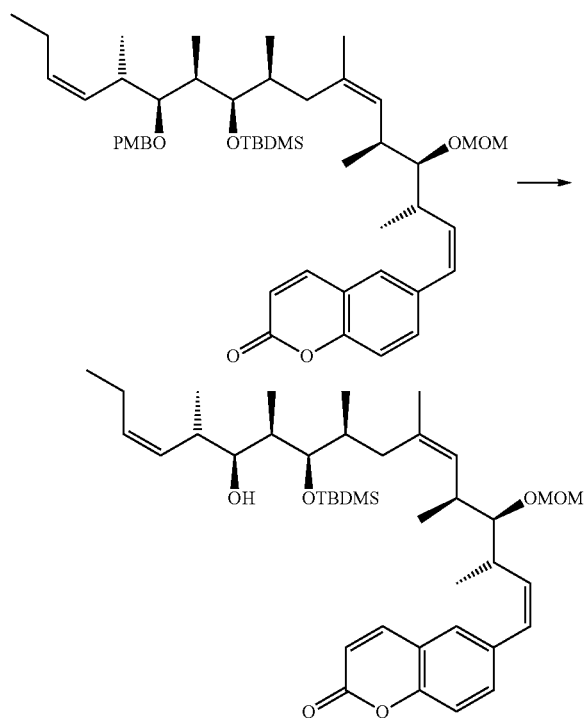

Using a similar deprotection procedure on a 0.015 mmol scale yielded the deprotected alcohol (0.009, 88%) as a colourless oil; [α]$^{589}_{21}$ +28.9 (c 0.80, CHCl$_3$); IR (CHCl$_3$) 3514, 2961, 2930, 2876, 1735, 1570, 1462, 1258, 1153, 1097, 1038, 834, 773 cm$^{-1}$; $^1$H nmr (400 MHz, CDCl$_3$): δ 7.70 (1H, d, J 9.5 Hz, H-3 or H-2), 7.49 (2H, m, H-7b, H-7), 7.27 (1H, d, J 8.5 Hz, H-6), 6.41 (1H, d, J 9.5 Hz, H-3 or H-2), 6.37 (1H, d, J 12.0 Hz, H-8), 5.74 (1H, dd, J 11.5, 10.5 Hz, H-9), 5.56 (1H, dt, J 11.5, 7.5 Hz, H-22), 5.19 (1H, dd, J 11.0, 10.0 Hz, H-21), 4.98 (1H, d, J 10.0 Hz, H-13), 4.70 (2H, s, OCH$_2$O), 3.58 (1H, dd, J 6.0, 3.0 Hz, H-17), 3.41 (3H, s, OCH$_3$), 3.24 (2H, m, H-19, H-11), 3.11-3.05 (1H, m, H-10), 2.65-2.54 (2H, m, H-20, H-12), 2.17 (1H, t, 1×H-15), 2.08 (2H, m, 2×H-23), 1.86-1.79 (1H, m, H-16), 1.76 (1H, td, J 7.0, 2.5 Hz, H-18), 1.61 (1H, m, 1×H-15), 1.48 (3H, s, H-14'), 1.06 (3H, d, J 7.0 Hz, H-10'), 0.99 (3H, t, J 7.5 Hz, H-24), 0.96 (6H, m, H-20', H-12'), 0.91 (3H, d, J 6.5 Hz, H-18'), 0.90 (9H, s, SiC(CH$_3$)$_3$), 0.70 (3H, d, J 7.0 Hz, H-16'), 0.08 (3H, s, 1×SiCH$_3$), 0.07 (3H, s, 1×SiCH$_3$); $^{13}$C nmr (100 MHz, CDCl$_3$): δ 160.8, 152.6, 149.3, 143.6, 139.0, 136.2, 134.2, 133.5, 132.3, 131.6, 129.9, 127.3, 126.6, 118.5, 116.7, 116.6, 98.4, 87.5, 79.0, 75.9, 56.1, 37.8, 36.5, 35.8, 35.6, 35.5, 34.6, 26.2 (3C), 23.1, 21.0, 18.5, 18.1, 17.2, 16.8, 14.4, 13.3, 9.5, −3.3, −3.6; m/z 691 [M+Na]$^+$ (Found [M+Na]$^+$, 691.4347, C$_{40}$H$_{64}$O$_6$Si requires [M+Na]$^+$ 691.4364).

Carbamate Formation

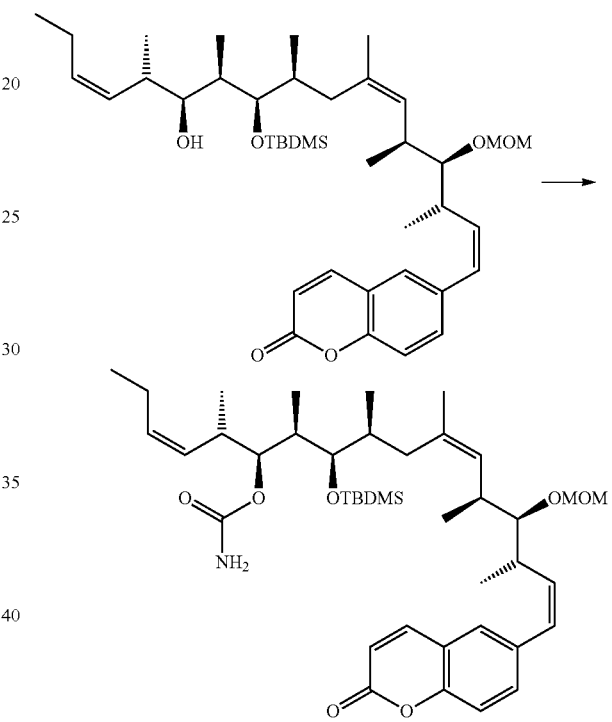

Using a similar carbamate formation procedure on a 0.12 mmol scale yielded the carbamate (0.007 g, 82%) as a colourless oil; [α]$^{589}_{22}$ +46.3 (c 0.65, CHCl$_3$); IR (CHCl$_3$) 3489, 3362, 2962, 2927, 2871, 1727, 1601, 1570, 1462, 1376, 1098, 1037, 833, 773 cm$^{-1}$; $^1$H nmr (400 MHz, CDCl$_3$): δ 7.02 7.73 (1H, d, J 9.5 Hz, H-3 or H-2), 7.47 (2H, m, H-7b, H-7), 7.28 (1H, m, H-6), 6.42 (1H, d, J 9.5 Hz, H-3 or H-2), 6.35 (1H, d, J 12.0 Hz, H-8), 5.74 (1H, dd, J 12.0, 10.5 Hz, H-9), 5.39 (1H, dt, J 11.0, 7.0 Hz, H-22), 5.27 (1H, dd, J 11.0, 10.0 Hz, H-21), 4.97 (1H, d, J 9.5 Hz, H-13), 4.70 (2H, s, OCH$_2$O), 4.67 (1H, t, J 6.0 Hz, H-19), 4.52 (2H, br s, NH$_2$), 3.41 (3H, s, OCH$_3$), 3.78 (1H, dd, J 4.5, 4.0 Hz, H-17), 3.21 (1H, dd, J 7.0, 4.5 Hz, H-11), 3.10-3.05 (1H, m, H-10'), 2.79 (1H, dt, J 9.5, 6.5 Hz, H-20'), 2.53 (1H, dt, J 10.0, 7.0 Hz, H-12'), 2.10-1.97 (3H, m, 2×H-23, 1×H-15), 1.86-1.78 (1H, m, H-18, H-16), 1.47 (1H, m, 1×H-15), 1.46 (3H, s, H-14'), 1.07 (3H, d, J 7.0 Hz, H-10'), 0.98 (3H, t, J 7.5 Hz, H-24), 0.95 (3H, d, J 6.5 Hz, H-20'), 0.94 (3H, d, J 7.0 Hz, H-12'), 0.90 (9H, s, SiC(CH$_3$)$_3$), 0.88 (3H, d, J 7.0 Hz, H-18'), 0.69 (3H, d, J 7.0 Hz, H-16'), 0.08 (3H, s, 1×SiCH$_3$), 0.05 (3H, s, 1×SiCH$_3$); $^{13}$C nmr (100 MHz, CDCl$_3$): δ 160.9, 156.9, 143.6, 136.1, 134.2, 133.3, 132.4, 132.2, 130.3, 129.9, 127.3, 126.6, 118.6, 116.7, 116.6, 116.0, 98.4, 87.6, 79.0, 56.1, 37.8, 36.0, 35.7, 35.5, 35.1, 33.9, 26.2 (3C), 22.9, 20.8, 185, 18.2, 17.9, 16.9, 14.4, 13.7, 10.2, −3.4, −3.7; m/z 734 [M+Na]+, 580 (Found [M+Na]+, 734.4430, $C_{41}H_{65}NO_7$ requires [M+Na]+ 734.4423).

Deprotection to the Final 6-Coumarin Compound

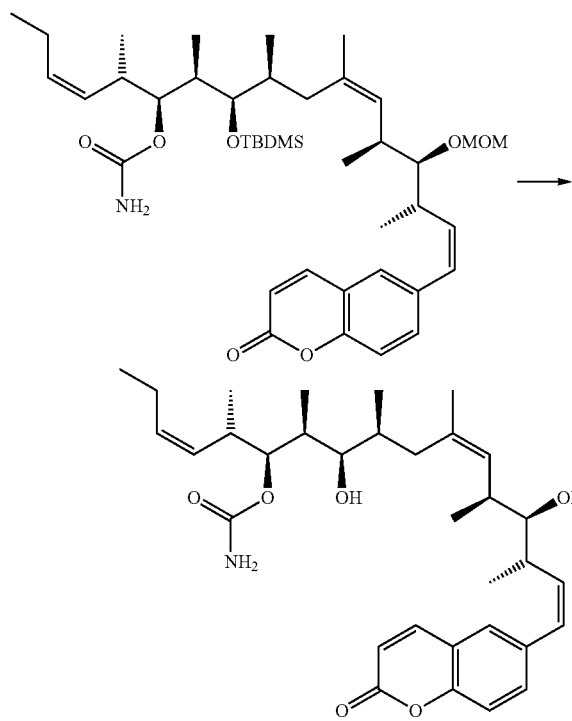

Using a similar deprotection procedure on a 0.010 mmol scale yielded that 6-coumarin compound (0.004 g, 56%) as a colourless oil; $[\alpha]^{589}{}_{22}$ +27.2 (c 0.35, $CHCl_3$); IR ($CHCl_3$) 3447, 3357, 2960, 2922, 2853, 1716, 1601, 1461, 1377, 1102, 1041, 990 cm$^{-1}$; $^1$H nmr (400 MHz, $CDCl_3$): δ 7.68 (1H, d, J 9.5 Hz, H-3 or H-2), 7.50 (1H, dd, J 8.5, 2.0 Hz, H-7), 7.44, (1H, d, J 2.0 Hz, H-7b), 7.28 (1H, d, J 8.5 Hz, H-6), 6.47 (1H, d, J 12.0 Hz, H-8), 6.43 (1H, d, J 9.5 Hz, H-3 or H-2), 5.74 (1H, dd, J 12.0, 10.5 Hz, H-9), 5.42 (1H, dt, J 11.0, 7.5 Hz, H-22), 5.27 (1H, dd, J 10.5, 9.0 Hz, H-21), 5.06 (1H, d, J 10.0 Hz, H-13), 4.71 (1H, dd, J 6.5, 4.5 Hz, H-19), 4.57 (1H, br s, $NH_2$), 3.30 (1H, t, J 5.5 Hz, H-11), 3.19 (1H, t, J 5.5 Hz, H-17), 3.01 (1H, m, H-10), 2.81 (1H, dt, J 9.5, 6.5 Hz, H-20), 2.54 (1H, dt, J 10.0, 6.5 Hz, H-12), 2.13-2.02 (2H, m, 2×H-23), 1.90-1.85 (3H, H-18, H-16, 1×H-15), 1.57 (1H, m, 1×H-15), 1.49 (3H, d, J 1.0 Hz, H-14'), 1.11 (3H, d, J 7.0 Hz, H-10'), 0.98 (3H, t, J 7.5 Hz, H-24), 0.96 (3H, d, J 6.5 Hz, H-20' or H-12'), 0.95 (3H, d, J 6.5 Hz, H-20' or H-12'), 0.91 (3H, d, J 7.0 Hz, H-18'), 0.78 (3H, d, J 6.0 Hz, H-16'); $^{13}$C nmr (100 MHz, $CDCl_3$): δ 160.7, 157.0, 152.7, 143.5, 135.2, 134.0, 133.7, 132.4, 132.3, 130.3, 129.4, 127.9, 127.5, 118.5, 116.8, 116.6, 79.6, 79.1, 76.4, 37.3, 35.8 (2C), 34.2, 33.7, 33.0, 23.1, 20.8, 18.2, 17.8, 16.2, 14.5, 13.8, 8.7; m/z 576 [M+Na]+, 536 [M+H—$H_2O$]+, 493, 473 (Found [M+Na]+, 576.3288, $C_{33}H_{47}NO_6$ requires [M+Na]+ 576.3296).

Pharmacological Data

Coumarin (+)-6 displayed nanomolar activity similar to (+)-discodermolide 1 against a wide range of cell lines, including breast (MCF-7) and ovarian (SKOV3), as well as the multi-drug resistant (MDR) cell line (NCI/ADR), which over-expresses the MDR efflux pump, P-glycoprotein. (Table 1). These results are particularly striking given that the entire C-1 to C-7 section has been replaced, including five of the 13 stereocenters.

23,24-Dihydro analogue (+)-8, displayed nanomolar activity equivalent to (+)-1 and (+)-6 in the antiproliferative assays over a series of cell lines.

Compounds (+)-9, (+)-10, (+)-11, and (+)-12 displayed micromolar activity against a wide range of cell lines, including breast (MCF-7) and ovarian (SKOV3), as well as the multi-drug resistant (MDR) cell line (NCI/ADR).

TABLE 1

Antiproliferative activities of the compounds

| Compound | Antiproliferative activity (nM) | | |
|---|---|---|---|
| | SKOV3 | MCF-7 | NCI/ADR |
| (+)-Discodermolide 1 | 25 | 26 | 260 |
| (+)-6 | 44 | 12 | 190 |
| (+)-8 | 35 | 15 | 230 |
| (+)-9 | 1800 | 1600 | 3300 |
| (−)-10 | 790 | 430 | 840 |
| (+)-11 | 2400 | 1600 | 3200 |
| (+)-12 | 2900 | 3000 | 4000 |

When ranges are used herein, such as carbon ranges or dosage ranges, all combinations and subcombinations of ranges and specific embodiments therein are intended to be included.

The disclosures of each patent, patent application and publication cited or described in this document are hereby incorporated herein by reference, in their entirety.

Those skilled in the art will appreciate that numerous changes and modifications can be made to the preferred embodiments of the invention and that such changes and modifications can be made without departing from the spirit of the invention. It is, therefore, intended that the appended claims cover all such equivalent variations as fall within the true spirit and scope of the invention.

What is claimed is:

1. A compound of formula I or Ia:

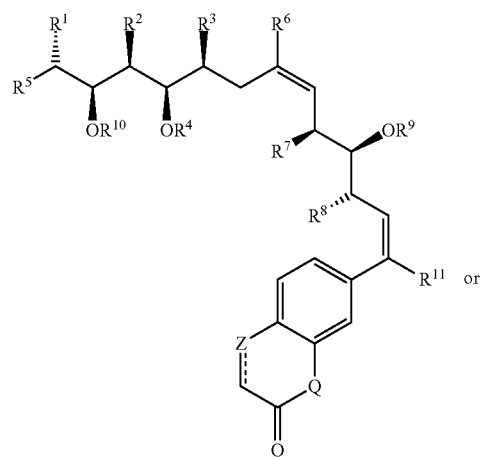

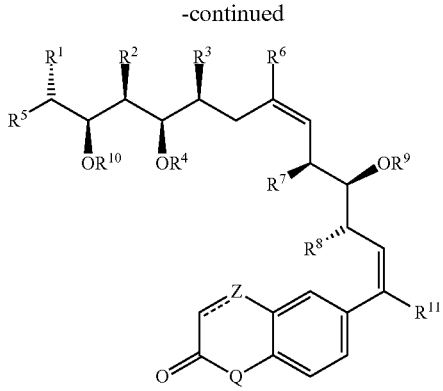

wherein:
- - - - represents the presence of a single bond or double bond;
$R^1, R^2, R^3, R^6, R^7, R^8$, and $R^{11}$ are each independently H or $C_{1-10}$alkyl;
$R^4$ and $R^9$ are each independently H or acid labile protecting group;
$R^5$ is $C_{2-6}$monoalkenyl or $C_{4-6}$alkadienyl;
$R^{10}$ is H, C(=O)NR$^{13}$R$^{14}$, or oxidatively labile hydroxyl protecting group;
Q is —O—;
Z is —CH— or —CH$_2$—, provided that when - - - - represents a double bond, then Z is —CH—;
$R^{12}$ is H, alkyl, or acid labile amino protecting group;
$R^{13}$ and $R^{14}$ are each independently H, $C_{1-10}$alkyl, $C_{2-6}$alkenyl, $C_{2-6}$alkynyl, OR$^c$, C(=O)R$^b$, S(O)$_p$R$^b$, (CH$_2$)$_r$C$_{3-12}$carbocycle, or (CH$_2$)$_r$heterocycle having 5 to 12 ring atoms; or $R^{13}$ and $R^{14}$ taken together with the nitrogen atom to which they are attached form a 5- or 6-membered heterocycle containing 0-3 additional heteroatoms selected from O, S, and N;
$R^b$ and $R^c$ are each independently H, $C_{1-6}$alkyl, $C_{2-6}$alkenyl, $C_{3-6}$cycloalkyl, or (CH$_2$)$_r$phenyl;
p is 1 or 2; and
each r is independently 0, 1, 2, 3, or 4;
or a pharmaceutically acceptable salt thereof.

2. The compound or its pharmaceutically acceptable salt of claim 1 having formula I.

3. The compound or its pharmaceutically acceptable salt of claim 2, wherein $R^1$, $R^2$, $R^3$, $R^6$, $R^7$, $R^8$, and $R^{11}$ are each independently H or $C_{1-3}$alkyl.

4. The compound or its pharmaceutically acceptable salt of claim 2, wherein $R^1$, $R^2$, $R^3$, $R^6$, $R^7$, $R^8$, and $R^{11}$ are each independently H or methyl.

5. The compound or its pharmaceutically acceptable salt of claim 2, wherein at least one of $R^4$ and $R^9$ is H.

6. The compound or its pharmaceutically acceptable salt of claim 5, wherein $R^4$ and $R^9$ are each H.

7. The compound or its pharmaceutically acceptable salt of claim 2, wherein $R^5$ is $C_{2-4}$-monoalkenyl or 1,3-butadien-1-yl.

8. The compound or its pharmaceutically acceptable salt of claim 2, wherein $R^5$ is

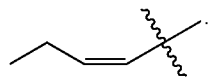

9. The compound or its pharmaceutically acceptable salt of claim 2, wherein $R^{10}$ is —C(=O)NR$^{13}$R$^{14}$ or oxidatively labile hydroxyl protecting group.

10. The compound or its pharmaceutically acceptable salt of claim 2 or, wherein $R^{10}$ is —C(=O)NR$^{13}$R$^{14}$.

11. The compound or its pharmaceutically acceptable salt of claim 1, wherein - - - - represents the presence of a carbon-carbon double bond.

12. The compound or its pharmaceutically acceptable salt of claim 10, wherein at least one of $R^{13}$ and $R^{14}$ is H.

13. The compound or its pharmaceutically acceptable salt of claim 10, wherein $R^{13}$ and $R^{14}$ are each H.

14. The compound or its pharmaceutically acceptable salt of claim 4, wherein $R^4$ and $R^9$ are each H.

15. The compound or its pharmaceutically acceptable salt of claim 1, having the structure:

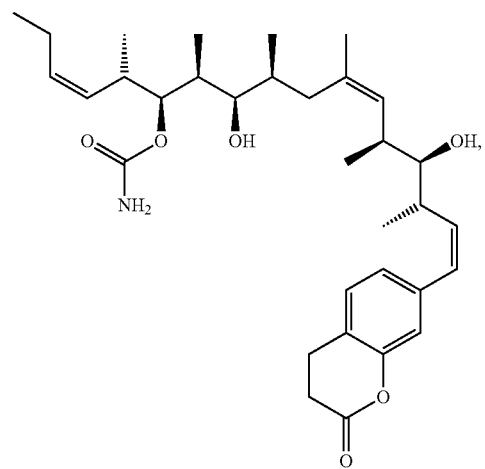

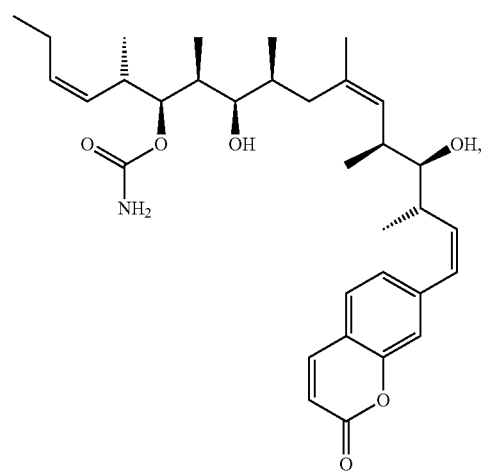

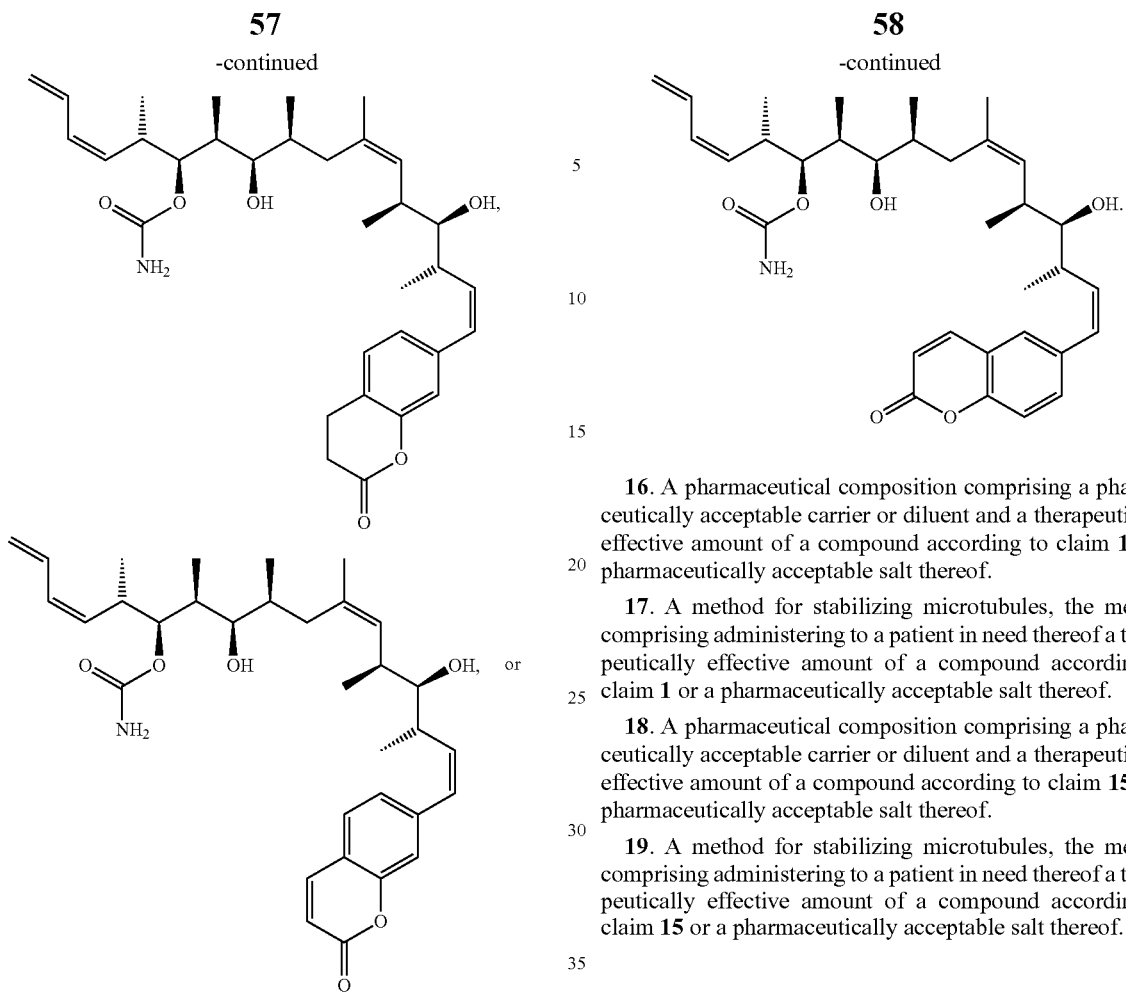

16. A pharmaceutical composition comprising a pharmaceutically acceptable carrier or diluent and a therapeutically effective amount of a compound according to claim 1 or a pharmaceutically acceptable salt thereof.

17. A method for stabilizing microtubules, the method comprising administering to a patient in need thereof a therapeutically effective amount of a compound according to claim 1 or a pharmaceutically acceptable salt thereof.

18. A pharmaceutical composition comprising a pharmaceutically acceptable carrier or diluent and a therapeutically effective amount of a compound according to claim 15 or a pharmaceutically acceptable salt thereof.

19. A method for stabilizing microtubules, the method comprising administering to a patient in need thereof a therapeutically effective amount of a compound according to claim 15 or a pharmaceutically acceptable salt thereof.

* * * * *